(12) United States Patent
Santos et al.

(10) Patent No.: US 8,372,379 B2
(45) Date of Patent: Feb. 12, 2013

(54) TECHNETIUM-99M (I) TRICARBONYL COMPLEXES WITH TRIDENTATE CHELATORS FOR MYOCARDIUM IMAGING

(75) Inventors: Isabel Rego Santos, Lisbon (PT); Antonio Manuel Rocha Paulo, Lisbon (PT)

(73) Assignee: Mallinckrodt LLC, Hazelwood, MO (US)

( * ) Notice: Subject to any disclaimer, the term of this patent is extended or adjusted under 35 U.S.C. 154(b) by 680 days.

(21) Appl. No.: 12/515,325

(22) PCT Filed: Nov. 23, 2007

(86) PCT No.: PCT/EP2007/010216
§ 371 (c)(1),
(2), (4) Date: May 18, 2009

(87) PCT Pub. No.: WO2008/061792
PCT Pub. Date: May 29, 2008

(65) Prior Publication Data
US 2010/0074842 A1    Mar. 25, 2010

(30) Foreign Application Priority Data

Nov. 24, 2006  (GB) .................................. 0623482.7

(51) Int. Cl.
*A61K 51/00*    (2006.01)
*A61M 36/14*    (2006.01)
(52) U.S. Cl. .................. 424/1.65; 424/1.37; 424/1.53; 424/9.42; 548/365.4; 548/365.1; 534/14; 534/10
(58) Field of Classification Search ................... 424/1.65
See application file for complete search history.

(56) References Cited

U.S. PATENT DOCUMENTS

| | | | |
|---|---|---|---|
| 5,112,594 A * | 5/1992 | Woulfe et al. ................ | 424/1.65 |
| 6,344,178 B1 | 2/2002 | Alberto et al. | |
| 7,188,725 B2 * | 3/2007 | Alberto et al. ................ | 206/363 |
| 2004/0018147 A1 | 1/2004 | Duatti et al. | |

FOREIGN PATENT DOCUMENTS

| | | |
|---|---|---|
| WO | WO 98/48848 | 11/1998 |
| WO | WO 00/50086 | 8/2000 |
| WO | WO 01/00637 | 1/2001 |
| WO | WO 03/077727 | 9/2003 |
| WO | WO 2004/091669 | 10/2004 |
| WO | WO 2005/077962 | 8/2005 |
| WO | WO 2006/080993 | 8/2006 |

OTHER PUBLICATIONS

Reger et al. J. Organomet. Chem. 658 (2002) 50-61.*
Reger et al. J. Organomet. Chem. 607 (2000) 120-128.*
Mltra et al. Pharmaceutical Research, 21 (7), 2004, 1153-1159.*
Jacobi et al. Eur. J. Inorg. Chem. 1998, 675-692.*
Database CA [Online], Chemical Abstracts Service, Columbus, Ohio, US; Zibaseresht et al., "Coordination chemistry of a terpyridine-tris(pyrasolyl) ditopic ligand", XP002471582 retrieved from STN Database accession No. 2005:1250454.
Database CA [Online], Chemical Abstracts Service, Columbus, Ohio, US; Reger et al., "Multitopic third generation tris(pyrazolyl)methane ligands built on alkyne structural scaffolding: first preparation of mixed tris(pyrazolyl)methane/tris(pyrazolyl)bora to ligands", XP002471583 retrieved from STN Database accession No. 2005:649019.
Reger et al., "Self-assembly of an organometallic silver (I) 1D architecture supported by three different types of bonding interactions", Inorganic Chemistry Communications, vol. 5, 2002, pp. 278-282, XP002471577.
Goodman et al., "Synthesis of tris(pyrazolyl)methanes of unprecendented complexity and functionality", Tetrahedron Letters, Elsevier, Amsterdam, NL, vol. 42, No. 1, Jan. 1, 2001, pp. 5-7, XP004227777.
Database CA [Online], Chemical Abstracts Service, Columbus, Ohio, US; Chen et al., "Copper(II/I) complexes of a bulky tris(pyrazolylmethyl)amine ligand", XP002471584 retrieved from STN Database accession No. 2000:691661.

(Continued)

*Primary Examiner* — Michael G Hartley
*Assistant Examiner* — Sean R Donohue

(57) ABSTRACT

Chelators of the formulae (I), (II) and (III) and tricarbonyl complexes of radioisotopes of Tc and Re bound to them, for use in myocardial imaging.

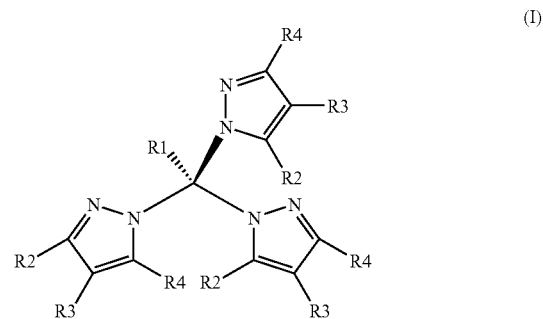

(I)

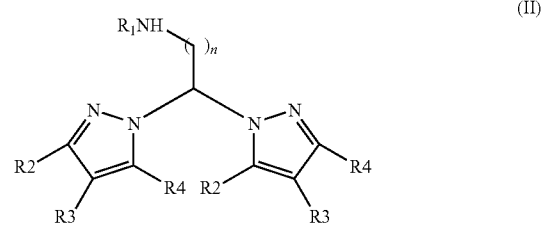

(II)

n = 1,2

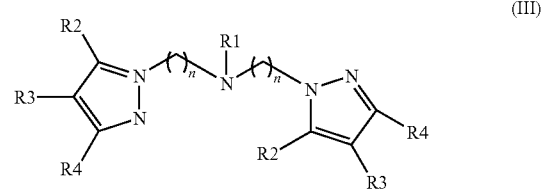

(III)

n = 1,2

22 Claims, 13 Drawing Sheets

OTHER PUBLICATIONS

Figure 1:
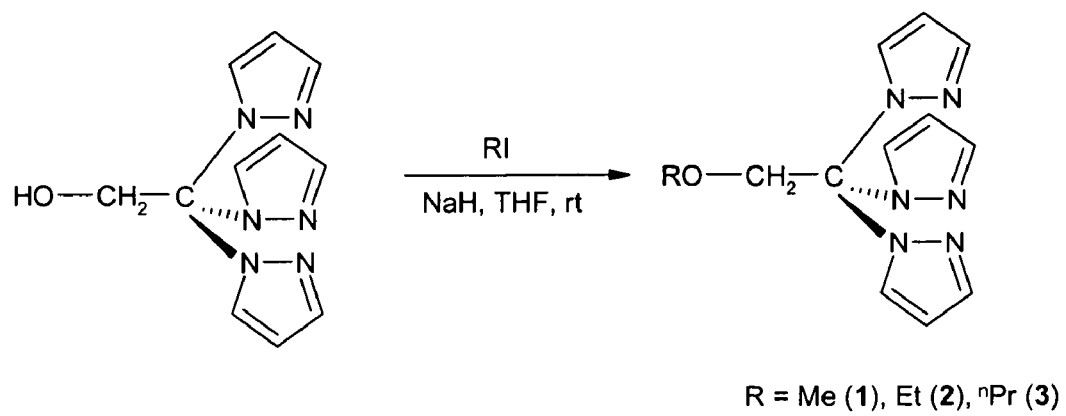

Reger et al., "Crystal Retro-Engineering: Structural Impact on Silver (I) Complex with Changing omplexity of ris(pyrazolyl)methane Ligands", Inorg. Chem., vol. 45, No. 19, Aug. 16, 2006, pp. 7758-7769, XP002471578.

Reger et al., "Influences of hanges in Jultitopic tris(pyrazolyl)methane Ligand Topology on Silver(I) Supramolecular Structures", Inorg. Chem., vol. 42, No. 12, 2003, pp. 3751-3764, XP002471579.

Reger et al., "Supramolecular Structures of Cadmium(II) Coordination Polymers: A New class of Ligands Formed by Linking Tripodal Tris(pyrazolyl)methane Units", Inorg. Chem., vol. 40, No. 24, 2001, pp. 6212-6219, XP002471580.

Reger et al., "Synthesis of Modified Tris(pyrazolyl)methane Ligands: Backbone Functionalization", Synthesis, No. 3, 2003, pp. 350-356, XP002471581.

Adhikari et al., "TI(I), Fe(II), and Co(II) Complexes Supported by a Monoanionic N,N,N-Heteroscorpionate Ligand Bias(3,5-ditertbutylpyrazol-1-yl)-1-CH2Nar (Ar=2,6-iPrsC6H3)" Inorganic Chemistry, 45(4), 1604-1610 CODEN: INOCAJ; ISSN: 0020-1699, 2006, XP002483603.

Brunet et al., A Simple Polyheterotopic Molecular Receptor Derived from Bispyrazolylmethane Showing Ambivalent Allosteric Cooperation of Zinc (II), Eur. J. Org. Chem., 2000, pp. 1913-1922, XP002483604.

Tang et al., "Synthesis and crystal structures of group 6 methal carbonyl complexes containing S-rich bis(pyrazol-1-yl)methane ligands", Journal of Organometallic Chemistry, Elsevier-Sequoia S.A. Lausanne, CH. vol. 649, No. 2, Apr. 22, 2002, pp. 152-160, XP004346388 ISSN: 0022-328X.

Sorrell et al., "Modeling the Active Site in Hemocyanin: Synthesis and Reactivity of binuclear Copper complex" Inorganica Acta, vol. 166, 1989, pp. 71-77, XP002483689.

Sorrell et al., "Synthesis of New Tripod Ligands Providing a Phenolate Donor. Structure of a Stable Monomeric Copper (I) Phenolate Complex", Inorg. Chem., vol. 25, No. 5, 1986, pp. 590-591, XP002483690.

Sorrell et al., "Synthesis and Characterization of Phenolate-Bridged Copper dimmers with a Cu-Cu Separation of >3.5A.Models for the Active Site of Oxidized Hemocyanin Derivatives", J. Am. Chem. Soc., vol. 107, 1985, pp. 4199-4206, XP002483691.

Alves et al., "Coordination Capabilities of Pyrazolyl Containing Ligands Towards the FAC-ÄRE(CO)3Ü+Moiety", Journal of the Chemical Society, Dalton Transactions, Chemical Society. Letchworth, GB, No. 24, Jan. 1, 2009, pp. 4714-4719, XP001179527 ISSN: 1472-7773.

Boschi et al., "A class of asymmetrical nitride $^{99m}$Tc heterocomplexes as heart imaging agents with improved biological properties", Nuclear Medicine Comm., 2002, 23, pp. 689-693.

Boschi et al., Synthesis and Biologic evaluation of Monocationic Asymmetric $^{99m}$Tc-Nitride heterocomplexes Showing High Heart Uptake and Improved Imaging Properties, Journal of Nuc. Med., May 2003, vol. 44, No. 5, pp. 806-814.

Maresca et al., "SAR Development of Ether-Containing Ligand Complexes of Tc(CO)$_3$ $^+$ for Cardiac Imaging", Technetium, Rhenium and Other Metals in chemistry and Nuclear Medicine7, 2006, pp. 399-402.

Bigmore et al., "Coordination, organometallic and related chemistry of tris(pyrazolyl)methand ligands", Dalton Trans., 2005, pp. 635-651.

Reger et al., "New N,N,N-Heteroscorpionates Based on 2,2-Bis(pyrazolyl)ethanamine and Its Derivatives. Ligands Designed for Probing Supramolecular Interactions," Inorganic chemistry, 2006, vol. 45, No. 11, pp. 4337-4339.

Alves et al., "Coordination capabilities of pyrazolyl containing ligands towards the fac[Re(CO)$_3$]$^+$ moiety", J. Chem. Soc., Dalton Trans., 2002, pp. 4714-4719.

Alves et al., "Pyrazolyl Derivatives as Bifunctional chelators for labeling tumor-Seeking Peptides with the *fac*-[M(CO)$_3$]+ Moiety (M=$^{99m}$Tc,Re): Synthesis, Characterization, and Biological Behavior", Bioconjugate hem., 2005, 16, pp. 438-449.

Herrick et al., "Aqueous preparation and physiological stability studies of Re(CO)$_3$(tripodal) compounds", Chem. Commun., 2006, pp. 4330-4331.

Liu et al., "Evaluation of novel cationic $^{99m}$Tc-nitrido complexes as radiopharmaceuticals for heart imaging: improving liver clearance with crown ether groups", Nucl. Med. and Biol., 33, 2006, pp. 419-432.

Bergmann et al., "Radiopharmaceuticals for Studying the Heart", Handboodk of Radiopharmaceuticals, 2003, pp. 529.

Duatti et al., "A Class of Asymmetrical Nitrido . . . ", Nucl. Med. Comm.., vol. 23, 2002, p. 689.

Duatti et al., "Synthesis and Biologic Evaluation of Monocationic Asymmetric . . . ", J. of Nucl. Med., vol. 44, 2003, p. 806.

Santos et al., "Rhenium and Technetium Complexes Anchored by Phosphines . . . ", Top. Curr. Chem.., 2005, vol. 252, pp. 45-84.

Alberto et al., New Organometallic Technetium Complexes for Radiopharmaceutical Imaging, Top. Curr. Chem., 2005, vol. 252, pp. 1-44.

Schenck et al., "Bimetallic Recativity. Synthesis of Bimetallic Complexes . . . ", Inorg. Chem., 1985, vol. 24, pp. 2334-2337.

Leonor et al., "Rhenium and Technetium Tricarbonyl complexes Anchored by Pyrazole-Based Tripods: Novel Lead Structures for the Design of Myocardial Imaging Agents", Retrieved from STN Database accession No. 2007:749128, XP002483605.

\* cited by examiner

R = Me (1), Et (2), $^n$Pr (3)

(11)

TECHNETIUM-99M (I) TRICARBONYL COMPLEXES WITH TRIDENTATE CHELATORS FOR MYOCARDIUM IMAGING

CROSS REFERENCE TO RELATED APPLICATIONS

This application is a national stage application of PCT/EP2007/010216, filed Nov. 23, 2007, which claims the benefit of UK Application No. GB 0623482.7 filed Nov. 24, 2006.

The present invention relates to the field of radiopharmaceuticals for diagnostic imaging, particularly of the myocardium, and provides cationic and lipophilic organometallic complexes of radioisotopes of Tc and Re, and preferably $^{99m}$Tc(I) organometallic complexes, which exhibit marked accumulation in the heart. These complexes contain a fac-[$^{99m}$Tc(CO)$_3$]$^±$ core and are anchored on novel pyrazolyl-containing tridentate chelators having at least one ether group, which are also within the scope of the invention. As these complexes accumulate in the myocardium, they are well suited for cardiovascular imaging.

In the field of cardiology, radioactive probes can provide information on the physiology and pathophysiology of the heart function, e.g. by myocardial perfusion, metabolism or innervation. Two $^{99m}$Tc radiopharmaceuticals, Sestamibi and Tetrafosmin, are commercially available and approved for myocardial perfusion studies. These radiopharmaceuticals, which consist respectively of lipophilic Tc(I) and Tc(V) cationic complexes, suffer from low heart/liver and heart/lung uptake ratios, and so are not entirely satisfactory for myocardial perfusion studies. We have therefore been seeking alternative and better performing $^{99m}$Tc complexes for myocardial imaging, profiting from the recently-introduced so-called organometallic labelling approach. This approach is based on complexes containing the fac-[$^{99m}$Tc(CO)$_3$]$^+$ core and is assuming a growing importance in the development of $^{99m}$Tc radioactive drugs for diagnostic medical applications.

We have now found that the combination of this organometallic core with appropriate ligands (appropriate in terms of charge, denticity or topology) provides cationic and lipophilic $^{99m}$Tc complexes with the biological properties required for myocardial imaging.

According to one aspect of this invention there are provided tridentate chelators of the type tris(pyrazolyl)methane (R$_1$C(pz*)$_3$) and bis(pyrazolyl)amine((pz*)$_2$CH(CH$_2$)$_n$NHR$_1$ or (pz*)(CH$_2$)$_n$NR$_1$(CH$_2$)$_n$(pz*)) of formulae (I), (II) and (III) respectively:

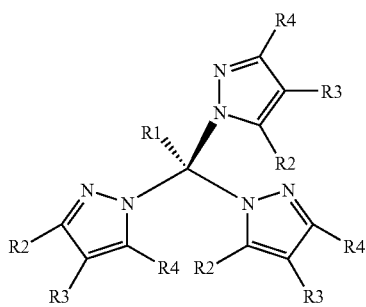

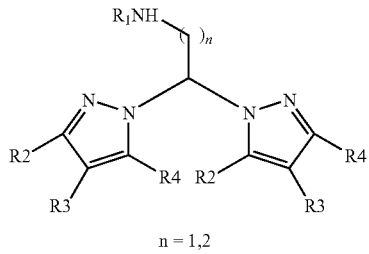

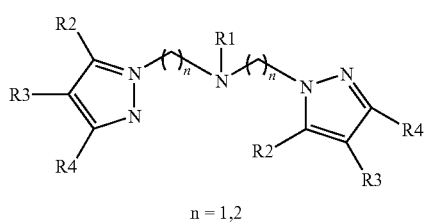

wherein each of R$_1$, R$_2$, R$_3$ and R$_4$ is independently hydrogen; a linear or branched, saturated or unsaturated C$_1$ to C$_9$ alkyl; a saturated or unsaturated carbocyclic group; a saturated or unsaturated heterocyclic or heteroaliphatic group with one or more atoms selected from O, N and S, wherein said carbocyclics, heterocyclics and heteroaliphatics are optionally substituted by one or more linear or branched, saturated or unsaturated C$_1$ to C$_9$ alkyls; an ether group —R$^X$—O—R$^Y$ or [(CH$_2$)$_x$O]$_y$(CH$_2$)$_z$ (x=2-3, y=3-8, z=2-5), wherein R$^X$ and R$^Y$ are independently linear or branched, saturated or unsaturated C$_1$ to C$_9$ alkyl, or saturated or unsaturated carbocyclics, any of which alkyl and/or carbocyclic groups may be substituted or unsubstituted, with the proviso that at least one of the substituents R$_1$, R$_2$, R$_3$ and R$_4$ is a linear or macrocyclic ether group of the type —R$^X$—O—R$^Y$ or [(CH$_2$)$_x$O]$_y$(CH$_2$)$_z$ (x=2-3, y=3-8, z=2-5), respectively, with the further proviso that when the tridentate chelator is of the type of formula (1), when R$_1$ is —R$^X$—O—R$^Y$ wherein R$^Y$ is substituted, and R$_2$, R$_3$, and R$_4$ are each H, R$^Y$ is not substituted apically by a further tris(pyrazolyl)methane moiety; and when R$_1$ is —R$^X$—O—R$^Y$ and R$_2$, R$_3$ and R$_4$ are each H, R$_1$ cannot be —CH$_2$—O—CH$_2$—(p-$^t$Bu-C$_6$H$_4$).

Preferably, the alkyl groups are each independently methyl, ethyl, n-propyl, i-propyl, n-butyl, t-butyl, n-pentyl, n-hexyl, n-heptyl, n-octyl, or n-nonyl.

More preferably, in each case, the alkyl groups are C$_1$ to C$_3$ alkyl groups, i.e. methyl, ethyl, n-propyl, and i-propyl.

If the alkyl and/or aryl groups are substituted, they may be substituted by one or more groups selected from alkyl, aryl, alkaryl, aralkyl, hydroxy, halogen, amino, nitro, alkoxy or carboxylic acid groups.

Preferably, if neither of R$_2$ and R$_4$ is an ether group, they are the same.

According to another aspect of the invention, R$_2$ and R$_4$ are both ether groups (linear or macrocyclic and preferably the same), in which case R$_3$ is preferably not an ether, but may be any of the other substituents listed above. In that case R$_1$ can be any of the substituents listed above, including an ether group that may be a different ether group from R$_2$ and R$_4$.

According to another aspect of the invention, R$_3$ is a linear or macrocyclic ether group. R$_2$ and R$_4$ are the same and can be any of the substituents listed above, but preferably not ether groups. In that case R$_1$ can also be any of the substituents listed above, including an ether group that may be the same or different from R$_3$.

The carbocyclic groups are preferably 5- or 6-membered rings, more preferably cyclopentyl, cyclohexyl or phenyl groups.

The heterocyclic groups are preferably 5- to 15-membered rings, more preferably containing oxygen, nitrogen, sulphur, or any combination thereof, and are most preferably macrocyclic ethers of the type $[(CH_2)_xO]_y(CH_2)_z$ (x=2-3, y=3-8, z=2-5, provided that x+y+z=5-15).

The heteroaliphatic groups preferably contain oxygen, nitrogen or sulphur atoms, or any combination thereof, and most preferably are ether groups of the type $—R^X—O—R^Y$, wherein $R^X$ and $R^Y$ are as defined above.

As can be seen from the above formulae, the linear or macrocyclic ether groups may be attached to the 3-, 4- and/or 5-positions of the pyrazolyl rings. Also, in formula (I) the ether group may be attached to the central carbon atom, in formula (II) to the terminal amine, and in formula (III) the ether group may be attached to the central nitrogen atom. In one embodiment, at least $R_1$ is an ether group in the respective formulae.

Preferably, the linear ethers are alkyl ethers, but they may also be aryl ethers or alkyl ethers which also contain an aryl substituent. Preferred ethers include those of the general formula $(CH_2)_nOR$, wherein n=1, 2 or 3, and R=methyl, ethyl or n-propyl.

The macrocyclic ethers are preferably crown ethers of the general formula $[(CH_2)_xO]_y(CH_2)_z$ (x=2-3, y=3-8, z=2-5).

The ligands shown in formulae (I), (II) and (III) above can stabilize cationic tricarbonyl complexes of the type fac-$[M(CO)_3(NNN)]^+$ (Re, $^{99m}$Tc), wherein NNN represents the tridentate chelator of any of the formulae I-III.

According to another aspect of the invention, there is provided a process for the preparation of tridentate chelators of formulae (I), (II) and (III), comprising contacting a compound of the formula

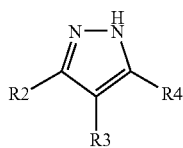

with a compound selected from a trihalomethane, a compound of the formula

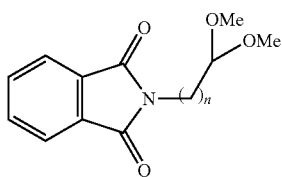

or a compound of the formula Hal-$(CH_2)_n$—$NR^1$—$(CH_2)_n$-Hal (wherein Hal=a halogen), and reacting a subsequent product with an alkyl halide, aryl halide, or a halide substituted ether compound,
wherein each of $R_1$, $R_2$, $R_3$ and $R_4$ is independently hydrogen; a linear or branched, saturated or unsaturated $C_1$ to $C_9$ alkyl; a saturated or unsaturated carbocyclic group; a group of formula $CO_2R_5$ or $(CH_2)_nOH$ wherein $R_5$ is independently hydrogen or a linear or branched, saturated or unsaturated $C_1$ to $C_9$ alkyl and n=1-6; a saturated or unsaturated heterocyclic or heteroaliphatic group with one or more atoms selected from O, N and S, wherein said carbocyclics, heterocyclics and heteroaliphatics are optionally substituted by one or more linear or branched, saturated or unsaturated $C_1$ to $C_9$ alkyls; an ether group $—R^X—O—R^Y$ or $[(CH_2)_xO]_y(CH_2)_z$ (x=2-3, y=3-8, z=2-5), wherein $R^X$ and $R^Y$ are independently linear or branched, saturated or unsaturated $C_1$ to $C_9$ alkyl, or saturated or unsaturated carbocyclics, any of which alkyl and/or carbocyclic groups may be substituted or unsubstituted, with the proviso that at least one of the substituents $R_1$, $R_2$, $R_3$ and $R_4$ is a linear or macrocyclic ether group of the type $—R^X—O—R^Y$ or $[(CH_2)_xO]_y(CH_2)_z$ (x=2-3, y=3-8, z=2-5), respectively, with the further proviso that when the tridentate chelator is of the type of formula (I), when $R_1$ is $—R^X—O—R^Y$ wherein $R^Y$ is substituted, and $R_2$, $R_3$, and $R_4$ are each H, $R^Y$ is not substituted apically by a further tris(pyrazolyl)methane moiety; and when $R_1$ is $—R^X—O—R^Y$ and $R_2$, $R_3$ and $R_4$ are each H, $R_1$ cannot be $—CH_2—O—CH_2—(p\text{-}^tBu\text{-}C_6H_4)$.

According to another aspect of the invention, tricarbonyl complexes of radioisotopes of Tc or Re bound to chelators of any of formulae (I), (II), or (III) above are also provided.

The radioisotope is preferably $^{99m}$Tc. The $^{99m}$Tc complexes can accumulate in the heart, therefore being useful in radiopharmaceuticals for myocardial imaging.

According to a further aspect of the invention there is provided a composition comprising a tridentate chelator as described above and a mixture of sodium boranocarbonate, sodium borate and sodium carbonate. Optionally, a transfer ligand may also be incorporated into the composition. Examples of such transfer ligands are salts of a weak organic acid, i.e. an organic acid having a pKa in the range 3 to 7, with a biocompatible cation. Such weak organic acids include acetic acid, citric acid, tartaric acid, gluconic acid, glucoheptonic acid, benzoic acid, phenols or phosphonic acids. Particularly, the transfer ligands comprise tartrate, gluconate, citrate, and/or glucoheptonate salts. Preferably, these compositions are in lyophilised form in a sterile vial.

There is also provided a composition comprising a tridentate chelator of any of formulae (I), (II), or (III) and a filler material. By filler material it is meant any material which can be combined with the composition to enable the formation of tablets or pellets of the composition. Exemplary filling materials include, but are not limited to, inositol, lactose and saccharose.

If desired, this composition may also contain an anti-oxidant substance, such as but not limited to gentisic acid, ascorbic acid or methionine.

There is also provided a process for the preparation of a tricarbonyl complex of radioisotopes of Tc or Re bound to chelators of any of formulae (I), (II), or (III), comprising contacting a compound of formula $[M(X)_3(CO)_3]^+$, wherein M=Tc or Re and X=$H_2O$, MeOH or a halogen, with a tridentate chelator in an alcoholic or aqueous solvent, at a pH of about 6 or less.

Alternatively, the compound of formula $[M(X)_3(CO)_3]^+$ can be contacted with a composition comprising a tridentate chelator of any of formulae (I), (II), or (III) and a mixture of sodium boranocarbonate, sodium borate and sodium carbonate.

The pH of the reaction is preferably about 4 or less, and the alcoholic solvent is preferably ethanol.

The compound of formula $[M(X)_3(CO)_3]^+$ can be prepared by adding $^{99m}$Tc-pertechnetate in saline (which is preferably obtained from a $^{99}$Mo/$^{99m}$Tc generator), or a perrhenate complex, to a composition comprising sodium boranocarbonate, sodium borate and sodium carbonate. An example of such a composition is IsoLink®, which comprises sodium boranocarbonate, sodium borate, sodium carbonate and a tartrate salt.

A general mode of preparation of the tricarbonyl complex of radioisotopes of Tc or Re bound to chelators of any of formulae (I), (II), or (III), involves a pertechnetate or perrhenate being added to a solution containing the mixture comprising sodium boranocarbonate, sodium borate and sodium carbonate, and this is then heated to yield the tricarbonyl precursor $[M(H_2O)_3(CO)_3]^+$ (M=Tc, Re). The solution (which has a pH of about 10.5) is acidified to about pH 4, mixed with a tridentate chelator ligand and heated again to allow the reaction between the tricarbonyl complex and the ligand.

The boranocarbonate-containing composition is used to reduce the pertechnetate (or perrhenate) from oxidation state VII to I and, at the same time, to generate carbon monoxide which will coordinate and stabilize the Tc(I) in $[Tc(H_2O)_3(CO)_3]^+$.

There is also provided a method of myocardial imaging comprising administering an imaging composition comprising an effective amount of a tricarbonyl complex of radioisotopes of Tc or Re bound to chelators of any of formulae (I), (II), or (III) to a patient. Preferably, the imaging composition is injected intravenously into the patient, who is either at rest or has undergone exercise prior to administration, where an assessment of myocardial bloodflow is necessary. SPECT or planar scintigraphy is then performed after a relevant period post injection and the results of the biodistribution of the radioactive compound in the myocardium are evaluated.

The inclusion of at least one ether substituent in the tridentate chelator compounds is important. Lipophilic and cationic $^{99m}$Tc complexes can cross the membranes of cardiac cells by free diffusion, and it is believed that their accumulation in the heart originates from negative mitochondrial membrane potentials. The ether substituents tune the lipophilicity of the complexes to improve both heart uptake and excretion kinetics, especially clearance from the liver, as the ether groups can increase the likelihood of the complex being metabolised by the liver. Such behaviour will improve the target-to-background ratios.

Some synthetic procedures for chelators of formulae (I) to (III) and for the respective organometallic complexes with rhenium and technetium are given in schemes 1 and 2 respectively.

Scheme 1 - General procedures for the synthesis of chelators of formulae I - III.

Chelators of Class I

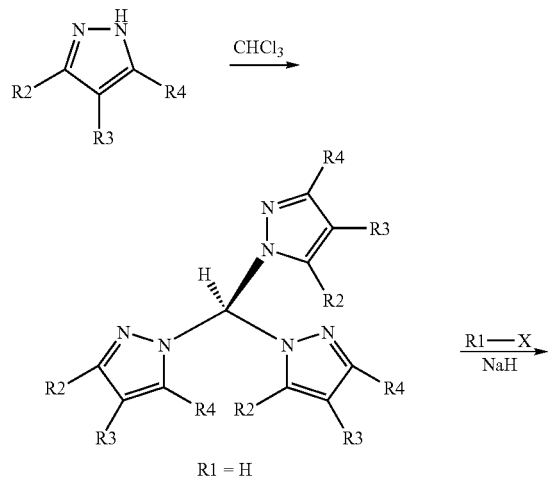

R1 = H

Chelators of Class II

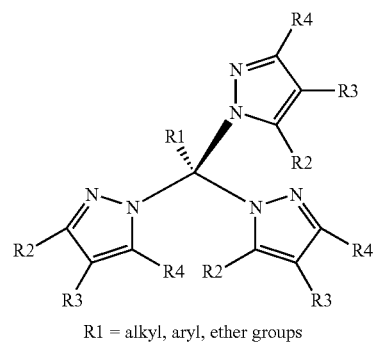

R1 = alkyl, aryl, ether groups

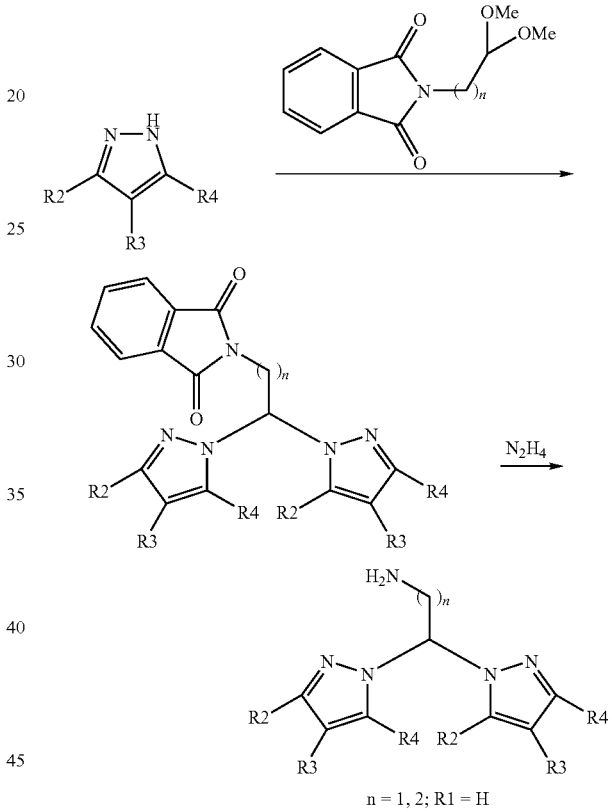

n = 1, 2; R1 = H n = 1, 2; R1 = alkyl, aryl or ether group

Chelators of Class III

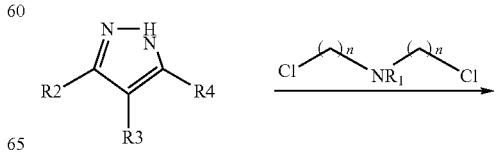

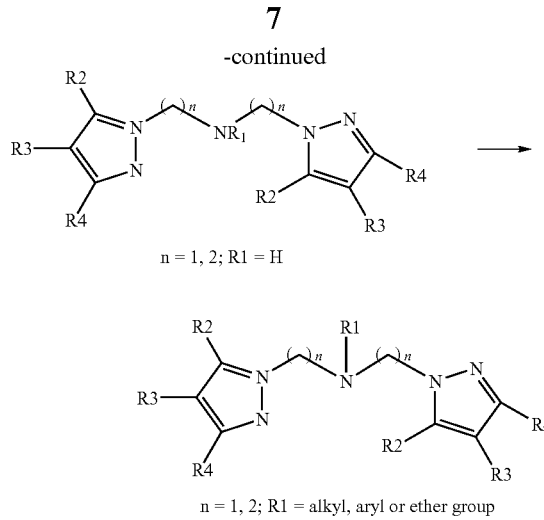

n = 1, 2; R1 = H n = 1, 2; R1 = alkyl, aryl or ether group

Figure 2:
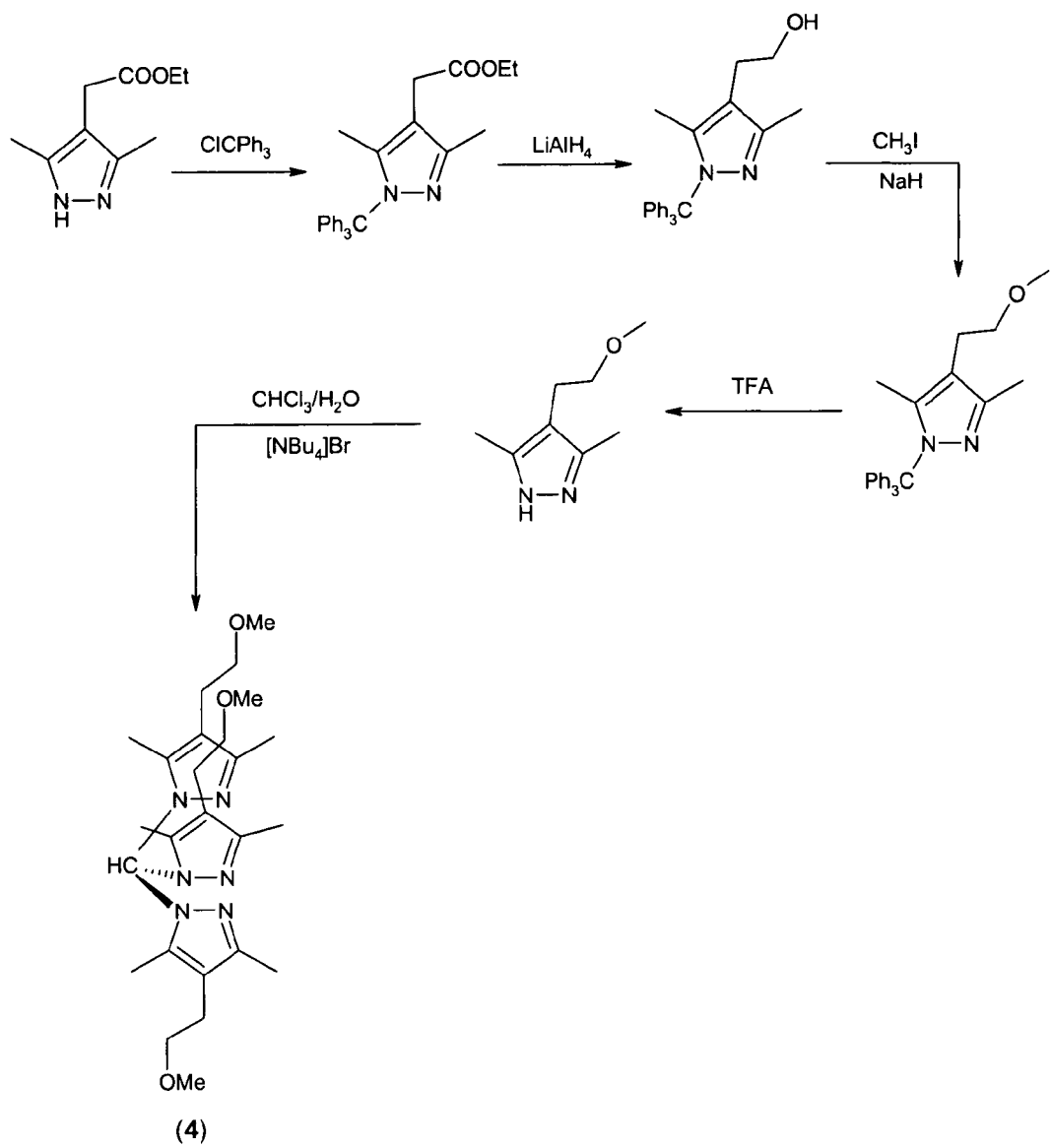

FIG. 2: Synthesis of representative examples of chelators of formula I bearing ether groups at 4-position of pyrazole.

Figure 3:
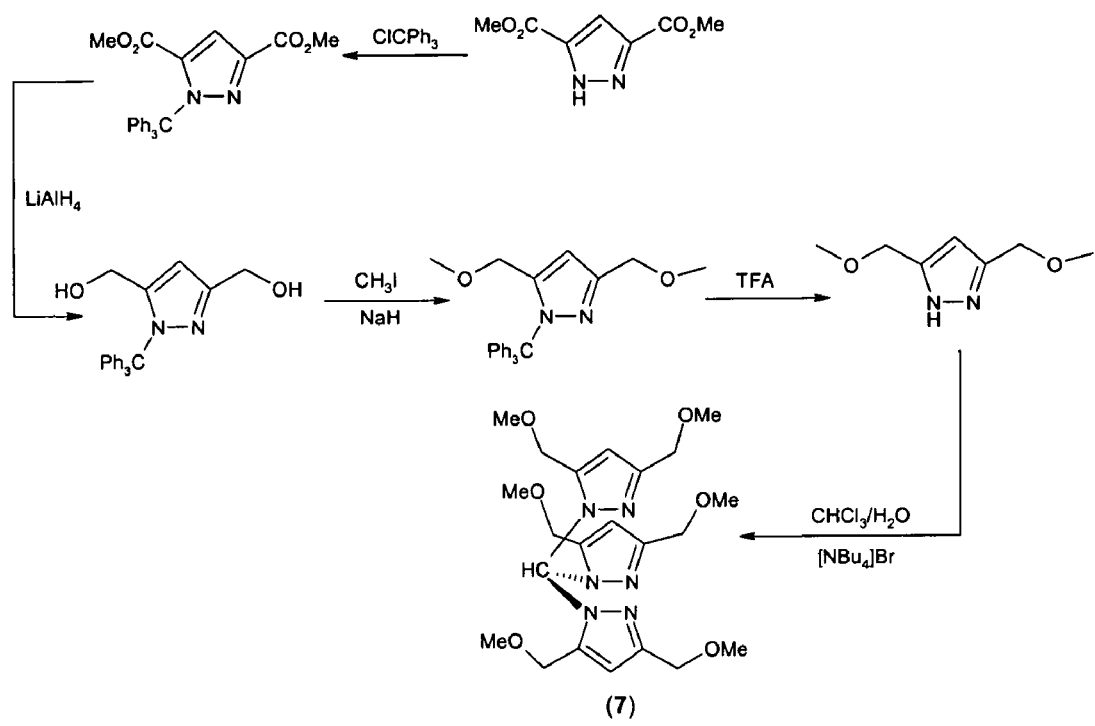

FIG. 3: Synthesis of a representative example of chelators of formula I having an ether group at the 3- and 5-positions of the pyrazolyl ring.

Figure 4:
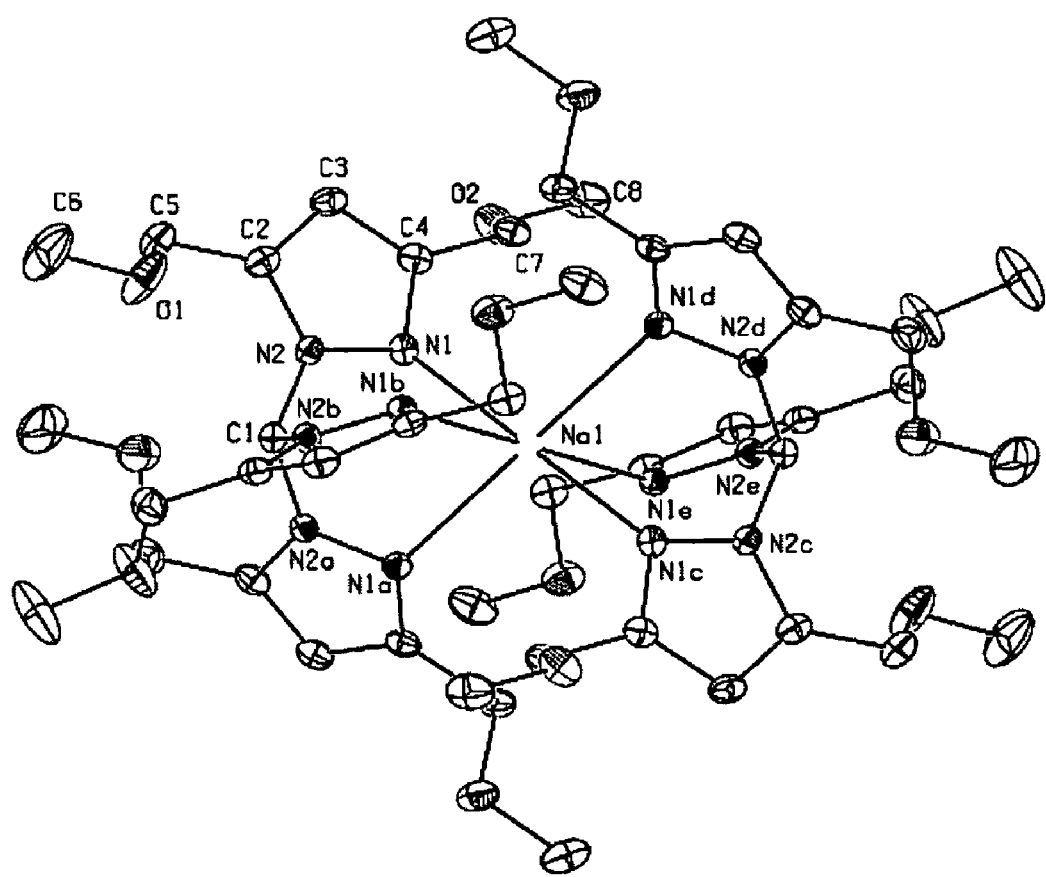

FIG. 4: ORTEP drawing of the cation of compound 8 ([{HC[3,5-$(CH_3OCH_2)_2$pz]$_3$}$_2$Na]+).

Figure 5:
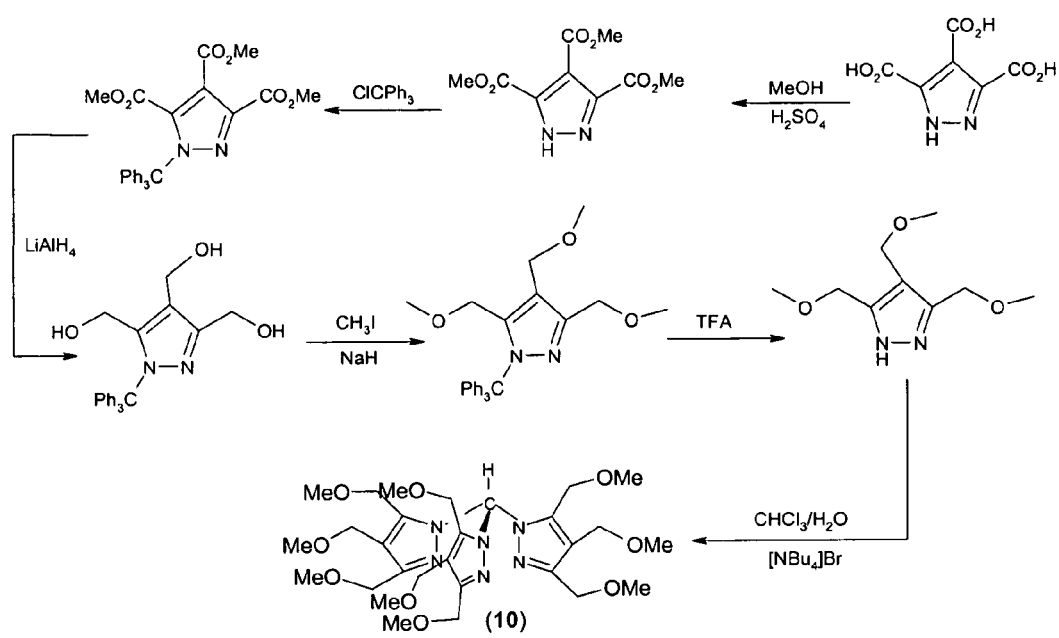

FIG. 5: Synthesis of a representative example of chelators of formula I having ether groups in the 3-, 4- and 5-positions of the pyrazolyl ring.

Figure 6:
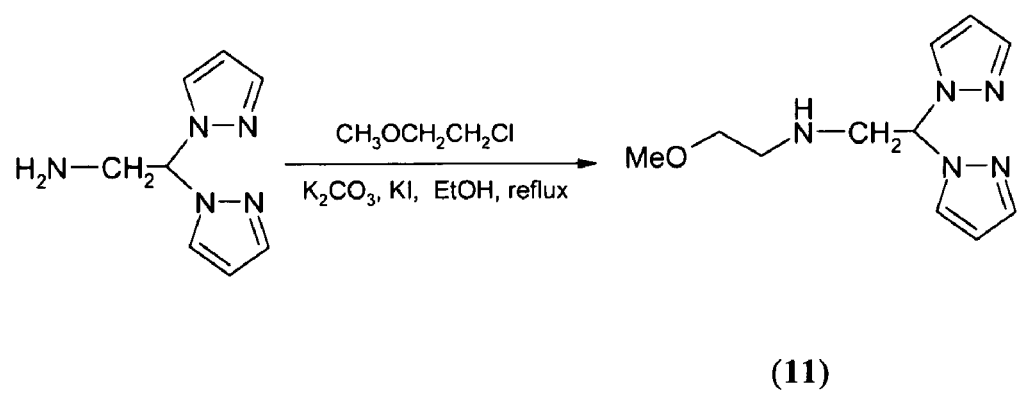

FIG. 6: Synthesis of a representative example of chelators of formula II having ether groups at the primary amine.

Figure 7:
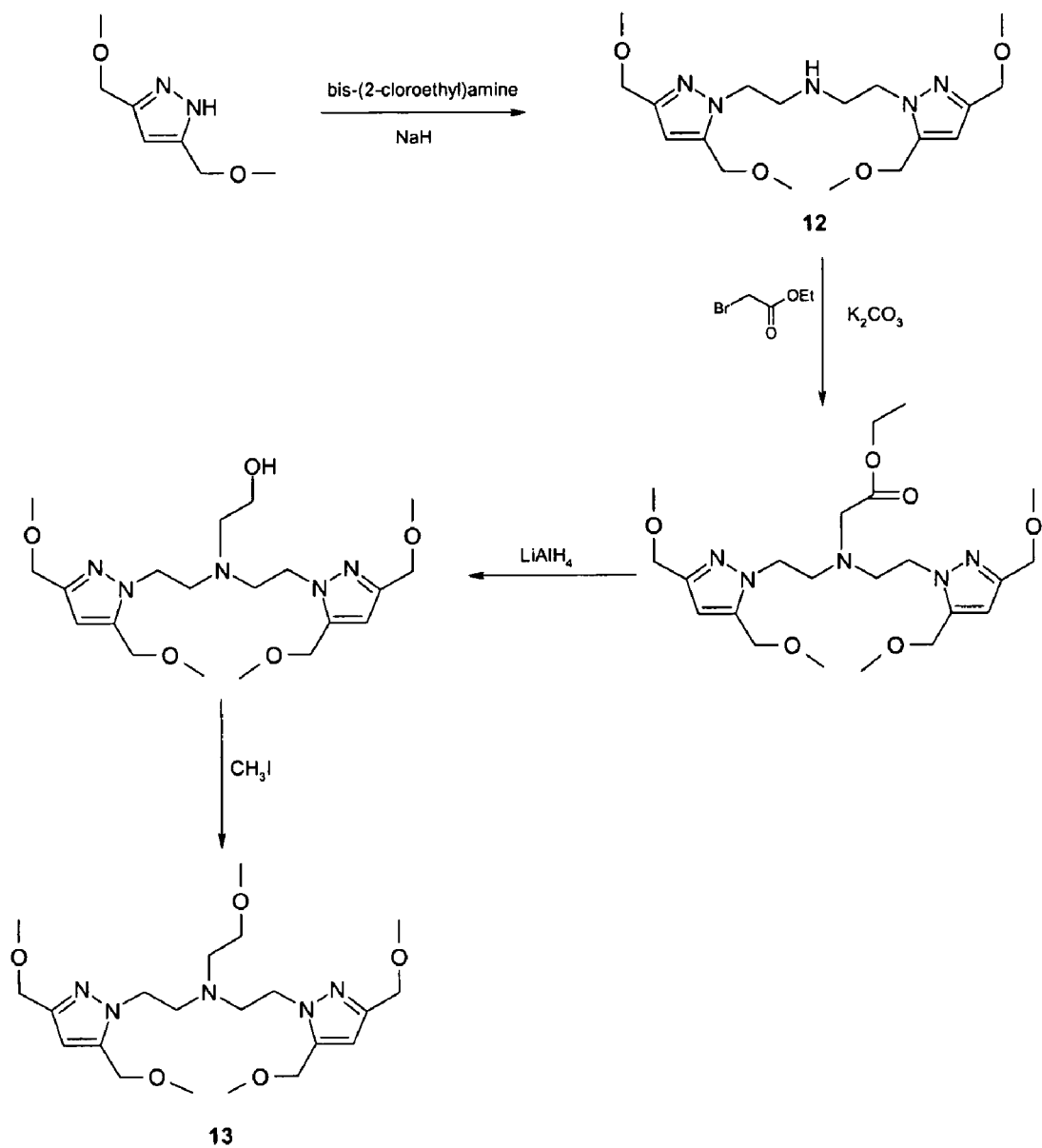

FIG. 7: Synthesis of a representative example of chelators of formula III having ether groups at the secondary amine and/or at the 3- and 5-position of the pyrazolyl rings.

Figure 8:
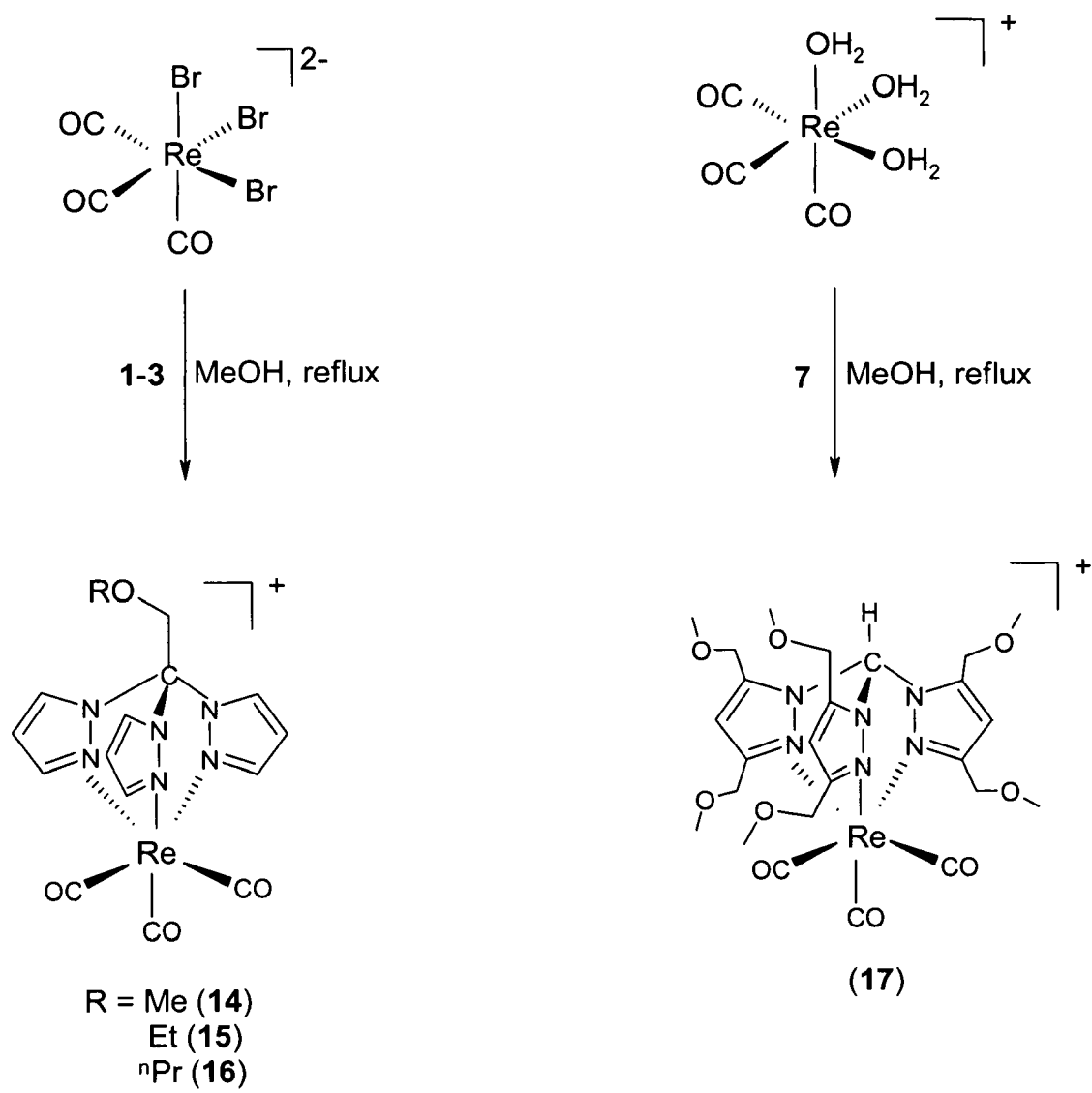

FIG. 8: Synthesis of Re complexes with a representative example of chelators of formula I.

Scheme 2 - General procedure for the synthesis of organometallic complexes with chelators of formulae (I) to (III).
In the scheme, M = $^{99m}$Tc or Re, and X may be MeOH, $H_2O$, or a halogen atom.

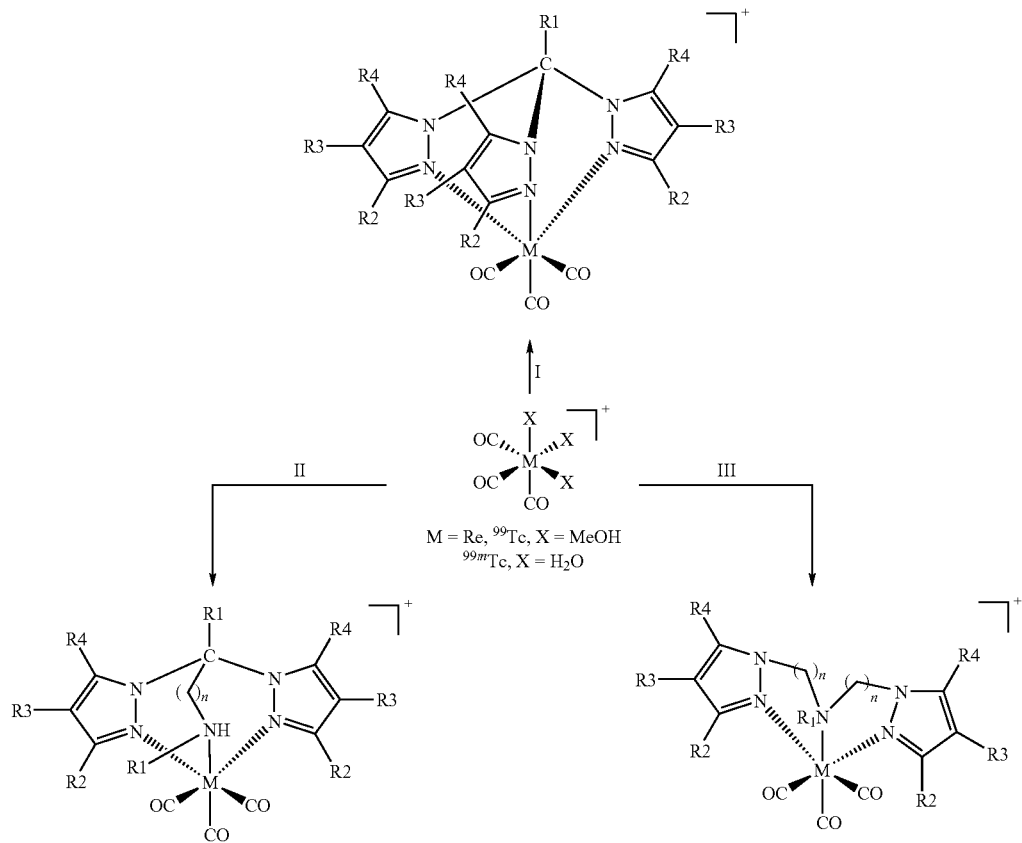

Some detailed but non-limiting examples are given below, showing how some of the chelators and their respective complexes with the fac-[M(CO)$_3$]$^+$ (where M=$^{99m}$Tc or Re) moieties may be synthesised, and demonstrating the affinity of such complexes for the myocardium.

Although $^{99m}$Tc is the preferred radionuclide in the invention, it will be understood by those skilled in the art that other radionuclides may be used.

In the examples reference is made to the following figures:

FIG. 1: Synthesis of representative examples of chelators of formula I having ether groups at the central carbon atom.

Figure 9:
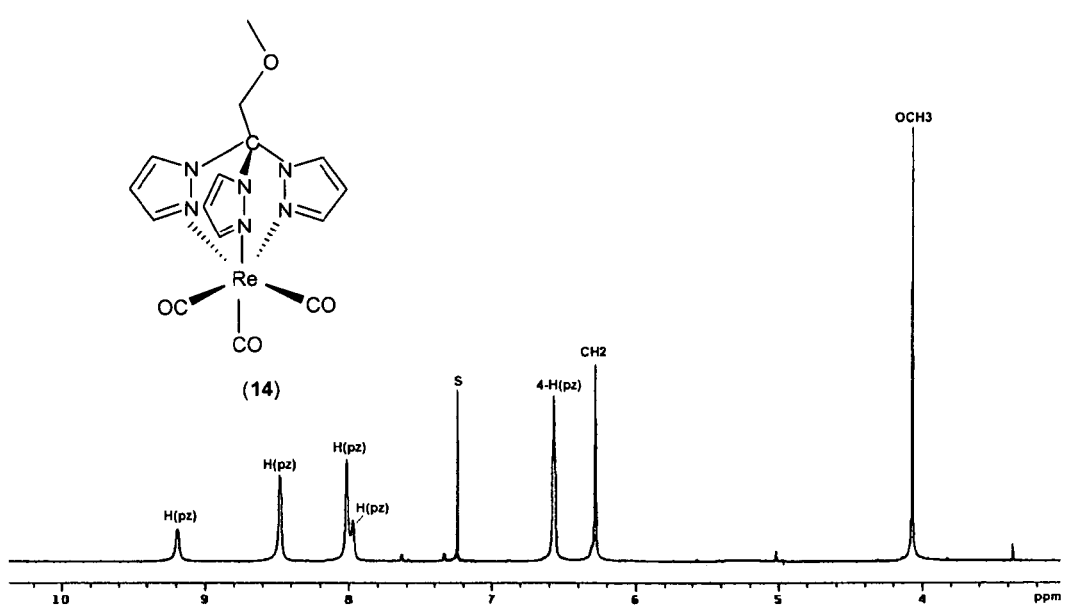

FIG. 9: $^1$H NMR spectrum of a rhenium complex with a chelator of formula I having an ether group at the central carbon atom.

Figure 10:
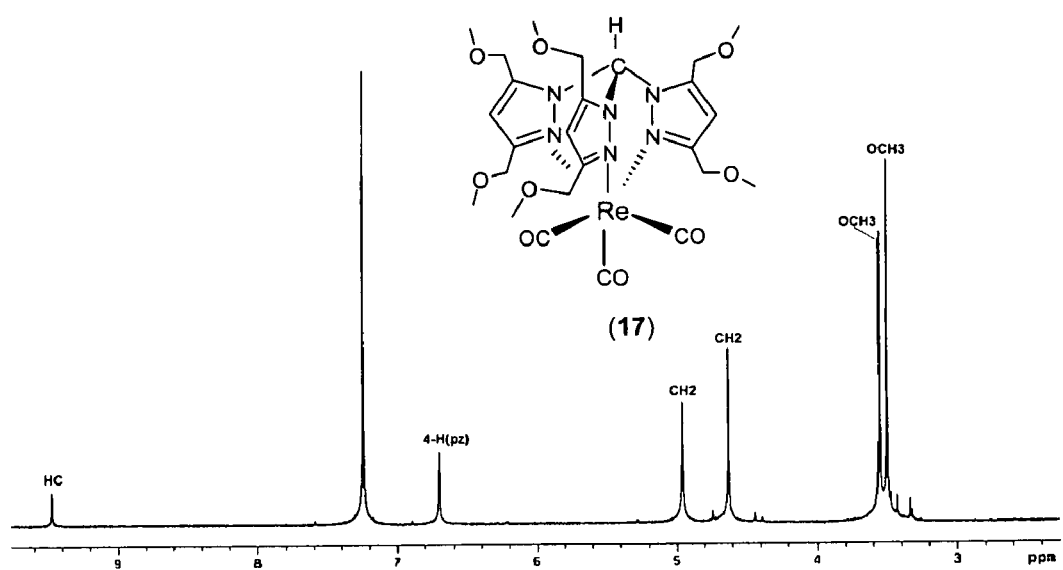

FIG. 10: $^1$H NMR spectrum in CDCl$_3$ of a rhenium complex with a chelator of formula I having ether groups at the 3- and 5-positions of the pyrazolyl rings.

Figure 11:
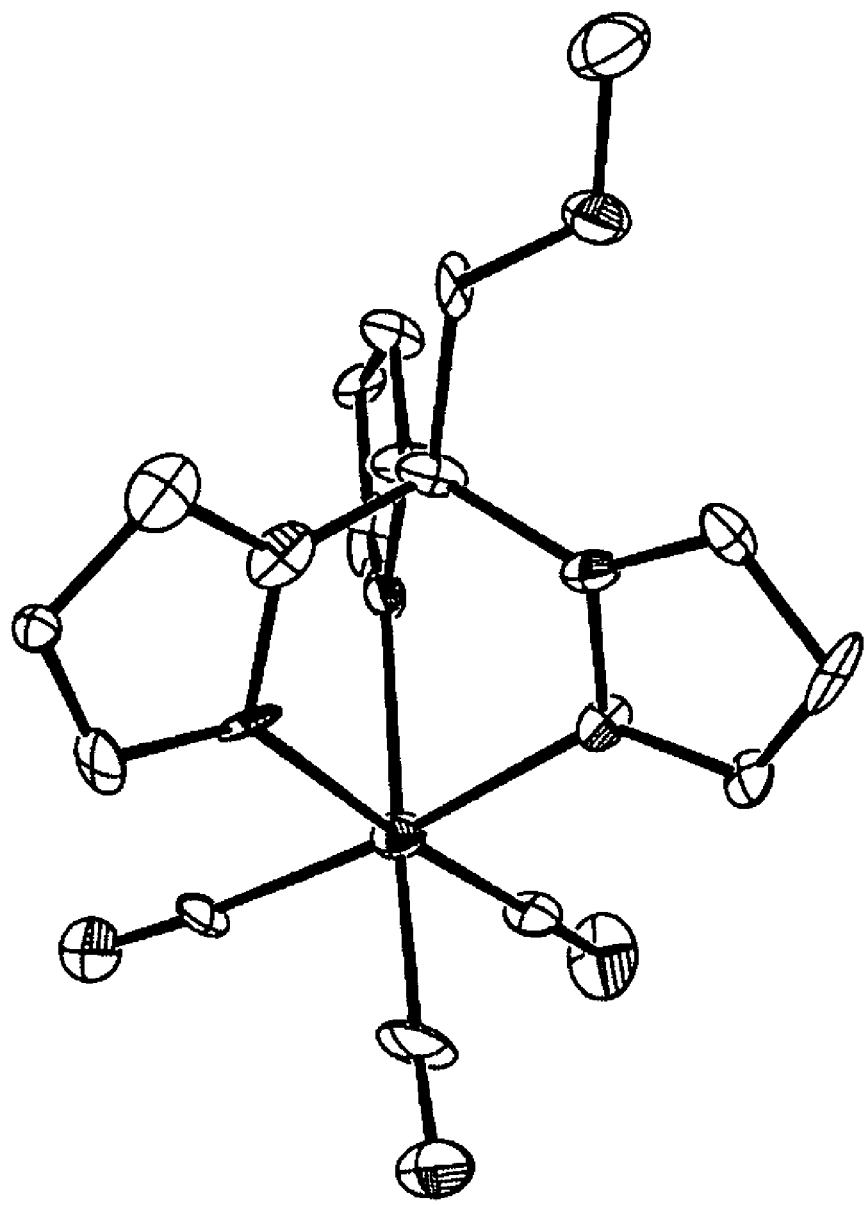

FIG. 11: Molecular structure of a Re(I) tricarbonyl complex with one of the chelators of class I.

Figure 12:
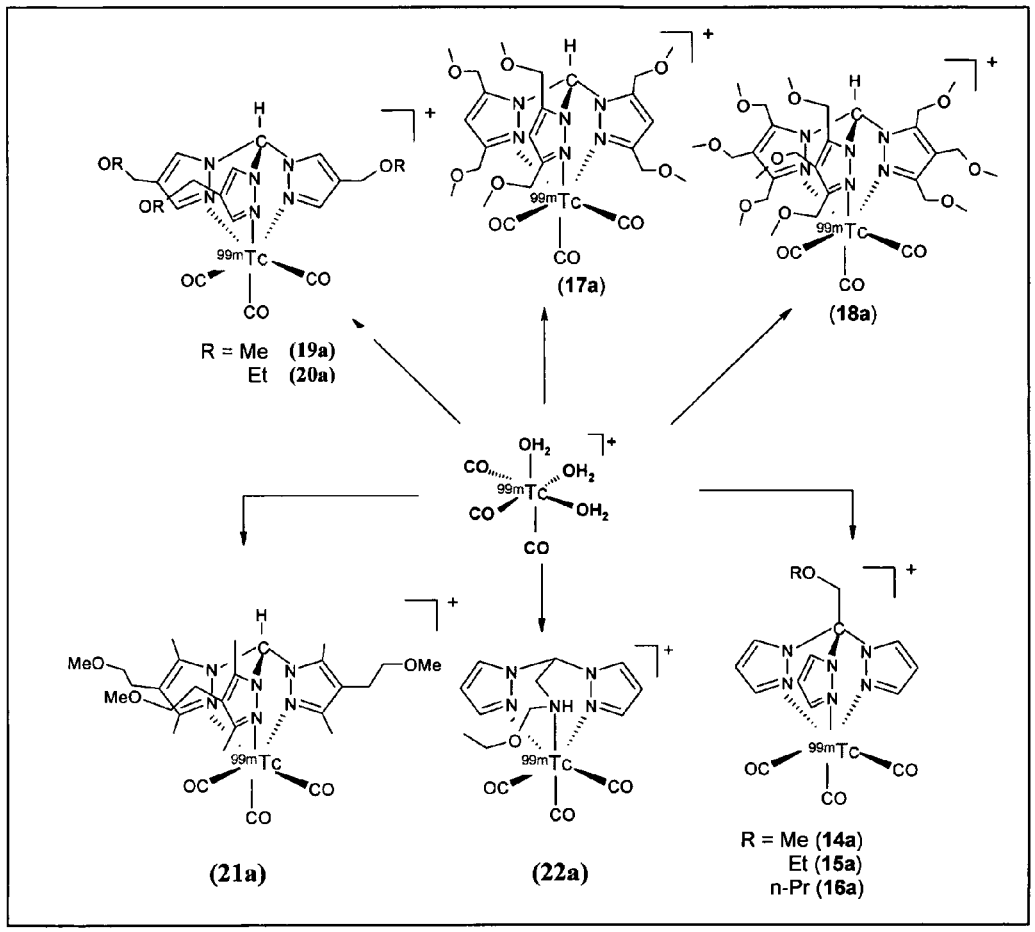

FIG. 12: Synthesis of $^{99m}$Tc(I) tricarbonyl complexes with chelators of formulae I and II.

Figure 13:
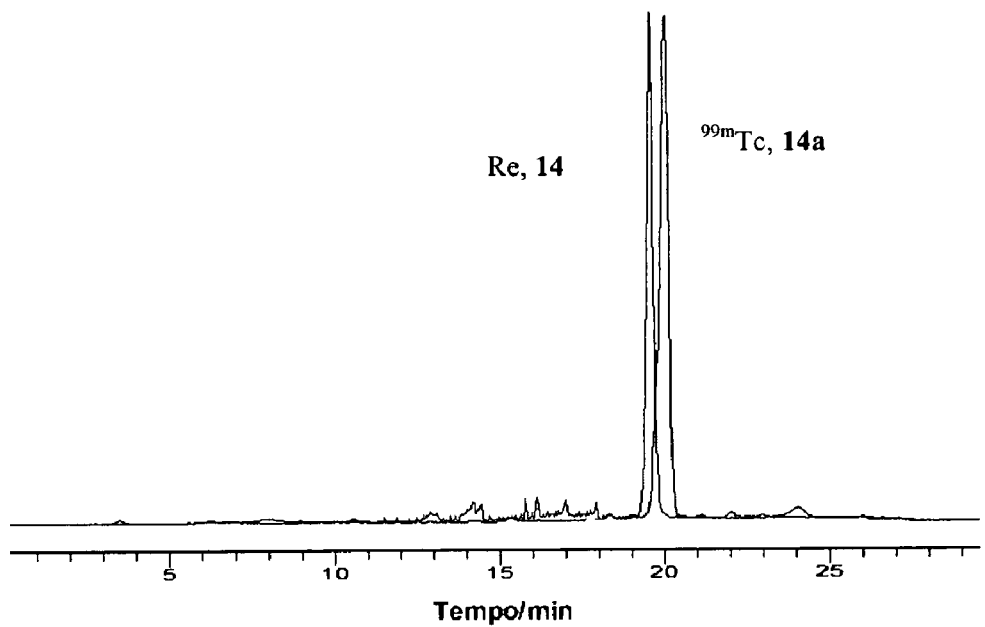

FIG. 13: HPLC chromatogram of a $^{99m}$Tc(I) tricarbonyl complex with a chelator of formula I and comparison with its Re congener.

EXAMPLES

Instruments

All chemicals and solvents were of reagent grade and were used without purification unless stated otherwise. $^1$H and $^{11}$C NMR spectra were recorded on a Varian Unity 300 MHz spectrometer; $^1$H and $^{11}$C chemical shifts (ppm) were referenced with the residual solvent resonances relative to tetramethylsilane. IR spectra were recorded on a Perkin-Elmer 577 spectrometer as KBr pellets. C, H and N analyses were performed on an EA 110 CE Instruments automatic analyser. Na[$^{99m}$TcO$_4$] was eluted from a Mallinckrodt Med. Inc. generator, using 0.9% saline. HPLC analysis of the complexes was performed on a Perkin-Elmer LC pump 200 coupled to a LC 290 tunable UV/Vis detector and to a Berthold LB-507A radiometric detector. Separations were achieved on a Nucleosil column (10 μm, 250 mm×4 mm), using a flow rate of 1 mL/min; UV detection, 254 nm.

Unless otherwise stated, reactions were carried out at normal pressure and under a nitrogen atmosphere. Work-ups were carried out in air.

Example 1

Production of Chelators of Formula I Having an Ether Group at the Central Carbon Atom The synthesis of this type of chelators was accomplished via deprotonation of 2,2,2-tris(pyrazolyl)ethanol followed by its reaction with adequate alkyl iodides (FIG. 1).

Example 1a

O-methyl-1,1,1-tris(pyrazolyl)ethanol: CH$_3$OCH$_2$C(pz)$_3$ (Compound 1)

To a stirred suspension of NaH (34 mg, 1.42 mmol) in THF (10 mL) was added, at room temperature (20-25° C.), 2,2,2-tris(pyrazolyl)ethanol (300 mg, 1.23 mmol) dissolved in the same solvent (10 mL), and the mixture was stirred for 1 h. After cooling to 0° C., a solution of methyl iodide (873 mg, 6.15 mmol) in THF (5 mL) was added dropwise. The resulting mixture was warmed to room temperature (20-25° C.) and stirred for about 16 h. After evaporation of THF under vacuum, the residue was extracted twice with 10 mL of diethyl ether. Following washing of the ether extracts with distilled water, compound 1 was recovered in the form of a colourless oil, after drying the organic phase under vacuum. Yield: 97% (307 mg, 1.19 mmol).

$^1$H NMR (CDCl$_3$, δ ppm): 7.64 (3H, d, H-5 (pz)), 7.34 (d, 3H, H-3 (pz)), 6.32 (dd, 3H, H-4 (pz)), 5.03 (s, 2H, CH$_2$), 3.38 (s, 3H, CH$_3$O). $^{13}$C NMR (CDCl$_3$, δ ppm): 141.3 (C-3 (pz)), 130.7 (C-5 (pz)), 106.5 (C-4 (pz)), 89.5 (C-(3z)$_3$), 75.5 (CH$_2$), 59.9 (CH$_3$O).

Example 1b

O-ethyl-1,1,1-tris(pyrazolyl)ethanol: CH$_3$CH$_2$OCH$_2$C(pz)$_3$ (Compound 2)

Compound 2 is a colourless oil with tendency to solidify on standing, which was obtained as above described for compound 1, starting from 305 mg (1.25 mmol) of 2,2,2-tris(pyrazolyl)ethanol. Yield: 66% (225 mg, 0.83 mmol).

$^1$H NMR (CDCl$_3$, δ ppm): 7.63 (3H, d, H-5 (pz)), 7.40 (d, 3H, H-3 (pz)), 6.31 (dd, 3H, 3H, H-4 (pz)), 5.05 (s, 2H, CH$_2$), 3.50 (q, 2H, OCH$_2$CH$_3$), 1.09 (tr, 3H, OCH$_2$CH$_3$). $^{13}$C NMR (CDCl$_3$, δ ppm): 141.2 (C-3 (pz)), 130.9 (C-5 (pz)), 106.4 (C-4 (pz)), 89.7 (C-(pz)$_3$), 73.5 (CH$_2$), 67.9 (CH$_2$), 15.0 (CH$_3$).

Example 1c

O-n-propyl-1,1,1-tris(pyrazolyl)ethanol: CH$_3$(CH$_2$)$_2$OCH$_2$C(pz)$_3$ (Compound 3)

Compound 3 is a colourless oil which was obtained as above described for compound 1, starting from 350 mg (1.43 mmol) of 2,2,2-tris(pyrazolyl)ethanol. Yield: 52% (212 mg, 0.74 mmol).

$^1$H NMR (CDCl$_3$, δ ppm): 7.63 (3H, d, H-5 (pz)), 7.40 (d, 3H, H-3 (pz)), 6.31 (dd, 3H, H-4 (pz)), 5.05 (s, 2H, CH$_2$), 3.40 (tr, 2H, OCH$_2$), 1.47 (m, 2H, CH$_2$), 0.77 (tr, CH$_3$).

Example 2

Production of Chelators of Formula I Having an Ether Group at the 4-Position of the Pyrazolyl Ring

Example 2a tris[3,5-Me$_2$-4-(2-methoxyethyl)pyrazolyl]methane, HC(3,5-Me$_2$-4-CH$_3$OCH$_2$CH$_2$pz)$_3$ (Compound 4)

FIG. 2

Ethyl 2-(3,5-dimethyl-1H-pyrazol-4-yl)acetate: To a solution of ethyl 3-acetyl-4-oxopentanoate (synthesized as described D. P. Shrout and D. A. Lightner, *Synth. Commun.* 20 (1990), 2075) (9.676 g, 51.96 mmol) in ethanol, at 0° C., was added slowly a solution of hydrazine hydrate (2.990 g, 59.75 g) in absolute ethanol. The reaction mixture was warmed to room temperature and stirred for 2 hours. After removing ethanol under vacuum, dichloromethane and water were added to the crude product and the organic layer was separated. The aqueous layer was extracted further with dichloromethane and the combined organic extracts were washed with water. After drying over MgSO$_4$ and evaporation of the solvent under reduced pressure, the pyrazole was isolated as a yellow oil. Yield: 72% (6.777 g, 37.2 mmol).

$^1$H NMR (300 MHz, CDCl$_3$, δ (ppm)): 4.09 (2H, q, 7 Hz, CH$_2$), 3.32 (2H, s, CH$_2$), 2.21 (6H, s, CH$_3$), 1.22 (3H, t, 7 Hz, CH$_3$). $^{13}$C NMR (75.37 MHz, CDCl$_3$, δ (ppm)): 171.5 (COOEt), 143.0 (C-pz), 108.6 (C-pz), 60.7 (CH$_2$), 29.4 (CH$_2$), 14.2 (CH$_3$), 10.9 (CH$_3$).

3,5-dimethyl-4-ethylacetate-1-tritylpyrazole: To a solution of 3,5-dimethyl-4-ethyl-acetatepyrazole (1.939 g, 10.6 mmol) in dry THF was added sodium hydride (556 mg, 60% in mineral oil, 13.8 mmol) and the mixture was stirred at room temperature for 1 hour. Triphenylmethyl chloride (2.955 g, 10.6 mmol) was then added, and the reaction run for 3 days at room temperature. After this time, the solvent was evaporated and the solid was stirred in water, filtered and washed with water and diethyl ether. After drying under vacuum the pyrazole was obtained as a solid. Yield: 46% (2.047 g, 4.82 mmol).

$^1$H NMR (300 MHz, CDCl$_3$, δ (ppm)): 7.30-7.00 (15H, m, Ph), 4.09 (2H, q, 7.2 Hz, CH$_2$), 3.29 (2H, s, CH$_2$), 2.15 (3H, s, CH$_3$), 1.42 (3H, s, CH$_3$), 1.20 (3H, t, 7 Hz, CH$_3$). $^{13}$C NMR (75.37 MHz, CDCl$_3$, δ (ppm)): 171.5 (COOEt), 144.7 (C-pz), 141.1 (Ph), 139.6 (C-pz), 130.3, 127.3, 127.1 (Ph), 111.6 (C-pz), 60.6 (CH$_2$), 30.0 (CH$_2$), 14.2 (CH$_3$), 13.0 (CH$_3$), 12.4 (CH$_3$).

3,5-dimethyl-4-hydroxyethyl-1-tritylpyrazole: To a solution of 3,5-dimethyl-4-ethylacetate-1-tritylpyrazole (2.442 g, 5.75 mmol) in dry THF, at 0° C., LiAlH$_4$ in ether (1M, 11.5 mmol) was added dropwise. After stirring at room temperature for about 16 h, the reaction was quenched by addition of water (1.4 ml) and NaOH (10%, 0.5 ml). The suspension was filtered off and the supernatant was extracted with dichloromethane. The organic phase was dried over MgSO$_4$ and vacuum dried, yielding the title compound as a yellow solid. Yield: 90% (1.980 g, 5.176 mmol).

$^1$H NMR (300 MHz, CDCl$_3$, δ (ppm)): 7.30-7.00 (15H, m, Ph), 3.60 (2H, t, 6.8 Hz, CH$_2$), 2.57 (2H, t, 6.8 Hz, CH$_2$), 2.15 (3H, s, CH$_3$), 1.41 (3H, s, CH$_3$).

3,5-dimethyl-4-ethyl methyl ether-1-tritylpyrazole: To a solution of 3,5-dimethyl-4-hydroxyethyl-1-tritylpyrazole (1.910 g, 4.99 mmol) in dry THF was added a portion of NaH (260 mg, 60% in mineral oil, 6.49 mmol), and the mixture was stirred at room temperature for about 16 h. Methyl iodide (1.56 mL, 24.95 mmol) was then added and the reaction stirred for 24 h at 20-25° C. After removal of THF under vacuum, the resulting residue was extracted with dichloromethane, followed by washing with water. Evaporation of dichloromethane under vacuum yielded the title compound as a yellow solid. Yield: 93% (1.834 g, 4.63 mmol).

$^1$H NMR (300 MHz, CDCl$_3$, δ (ppm)): 7.30-7.00 (15H, m, Ph), 3.32 (2H+3H, CH$_2$+OCH$_3$), 2.56 (2H, t, 7.8 Hz, CH$_2$), 2.15 (3H, s, CH$_3$), 1.40 (3H, s, CH$_3$).

3,5-dimethyl-4-ethyl methyl etherpyrazole: A solution of 3,5-dimethyl-4-ethyl methyl ether-1-tritylpyrazole (1.832 g, 4.62 mmol) in dichloromethane/methanol (1:2, 72 mL) was treated with CF$_3$COOH (18 ml) and heated at 75° C. for about 16 h. After this time, the mixture was cooled to room temperature and the solvents were evaporated. The crude product was purified by silica-gel chromatography using gradient elution, from 10% n-hexane/90% ethyl acetate to 20% methanol/80% ethyl acetate. After evaporation of the solvent from the collected fractions, the isolated pyrazole contained solvated CF$_3$COOH. To remove the acid, the compound was redissolved in ethyl acetate and washed successively with a saturated solution of NaHCO$_3$ and with water. After drying the organic phase over MgSO$_4$ and evaporation of the solvent under vacuum, the title compound was isolated as a slightly yellow oil. Yield: 43% (305 mg, 1.98 mmol).

$^1$H NMR (300 MHz, CDCl$_3$, δ (ppm)): 3.36 (2H, t, 7.2 Hz, CH$_2$), 3.32 (3H, s, OCH)), 2.60 (2H, t, 7.2 Hz, CH$_2$), 2.19 (6H, s, CH$_3$). $^{13}$C NMR (75.37 MHz, CDCl$_3$, δ (ppm)): 142.5 (C-pz), 111.7 (C-pz), 72.8 (CH$_2$), 58.56 (OCH$_3$), 23.7 (CH$_2$), 10.8 (CH$_3$).

HC(3,5-Me$_2$-4-CH$_3$OCH$_2$CH$_2$pz)$_3$ (compound 4): Under vigorous stirring, Na$_2$CO$_3$ (1.259 g, 1.88 mmol) was slowly added to a mixture of 3,5-dimethyl-4-ethyl methyl etherpyrazole (300 mg, 1.9 mmol) and tetrabutyl ammonium bromide (31.3 mg, 0.097 mmol) in H$_2$O (2.6 ml), occurring a slightly exothermic reaction. After cooling to room temperature (20-25° C.), 1.3 mL of chloroform was added and the resulting mixture was heated at reflux for 3 days. After this time, the solids formed were filtered off and 25 mL of CHCl$_3$ were added to the supernatant and the organic phase separated. The organic phase was washed with water, dried over MgSO$_4$ and the solvent was removed under vacuum. The residue obtained was purified by silica-gel chromatography (2% methanol/98% CHCl$_3$) to give the tris(pyrazolyl)methane as a slightly yellow oil which crystallised at room temperature. Yield: 31% (0.195 mmol, 92 mg).

$^1$H NMR (300 MHz, CDCl$_3$, δ (ppm)): 8.02 (1H, s, CH), 3.32 (6H, t, 7.5 Hz, CH$_2$), 3.30 (9H, s, OCH)), 2.57 (6H, t, 7.5 Hz, CH$_2$), 2.13 (9H, s, CH$_3$), 1.89 (9H, s, CH$_3$). $^{13}$C NMR (75.37 MHz, CDCl$_3$, δ (ppm)): 147.8 (C-pz), 138.1 (C-pz), 114.7 (C-pz), 81.2 (CH), 72.6 (CH$_2$), 58.6 (OCH$_3$), 24.1 (CH$_2$), 12.3 (CH$_3$), 9.2 (CH$_3$).

Example 2b

Tris(4-methoxymethylpyrazolyl)methane: HC(4-CH$_3$OCH$_2$pz)$_3$ (Compound 5)

Ethyl 1-tritylpyrazole-4-carboxylate: Ethyl pyrazole-4-carboxylate (W. Holtzer, G. Seiringer, J. Heterocyclic Chem., 1993, 30, 865) (1.7 g, 12.1 mmol) and NaH (680 mg, 60% in mineral oil, 16.94 mmol) reacted in dry DMF for 1 h. Then, trityl chloride (3.373 g, 12.1 mmol) was added, and the reaction mixture stirred for 3 days at room temperature. The title compound was recovered as described in example 2a for 3,5-dimethyl-4-ethylacetate-1-tritylpyrazole. Yield: 82% (3.79 g, 4 mmol).

$^1$H NMR (CDCl$_3$, δ ppm): 8.02 (1H, s, H-3 (pz)), 7.91 (1H, s, H-5 (pz)), 7.40-7.27 (9H, m, Ph), 7.20-7.00 (6H, m, Ph), 4.25 (2H, q, 7.2 Hz, CH$_2$), 1.29 (3H, t, 7.2 Hz, CH$_3$). $^{13}$C NMR (CDCl$_3$, δ ppm): 163.2 (CO), 142.3 (3/5-C(pz)), 141.1 (C-Ph)), 135.6 (C-Ph), 130.0 (C-Ph), 127.9 (C-Ph), 113.8 (4-C(pz)), 79.4 (N—CPh3), 60.2 (CH$_2$), 14.4 (CH$_3$).

1-trityl-4-hydroxymethylpyrazole: The title compound was obtained by reduction of ethyl 1-tritylpyrazole-4-carboxylate (3.785 g, 9.9 mmol) with LiAlH$_4$ (19.8 mmol) in dry THF (50 mL), as described in example 2a for the synthesis of 3,5-dimethyl-4-hydroxyethyl-1-tritylpyrazole. Yield: 91% (3.06 g, mmol).

$^1$H NMR (CDCl$_3$, δ ppm): 7.65 (1H, s, H-3 (pz)), 7.37 (1H, s, H-5 (pz)), 7.24-7.30 (9H, m, Ph), 7.08-7.16 (6H, m, Ph), 4.54 (2H, s, CH$_2$). $^{13}$C NMR (CDCl$_3$, δ ppm): 143.1 (3/5-C (pz)), 139.1 (C-Ph), 131.3 (C-Ph), 130.1 (C-Ph), 127.7 (C-Ph), 120.0 (4-C(pz)), 56.2 (CH$_2$).

1-trityl-4-methoxymethylpyrazole: This compound is obtained by reacting 1-trityl-4-hydroxymethylpyrazole (555 mg; 1.63 mmol) in dry tetrahydrofuran with sodium hydride (98 mg; 2.44 mmol) and iodomethane (0.5 mL; 8.15 mmol). Yield: 93% A) (536 mg, 1.51 mmol).

$^1$H NMR (CDCl$_3$, δ ppm): 7.63 (1H, s; 3-H(pz)), 7.36 (1H, s, 5-H(pz)), 7.25-7.30 (9H, m, Ph), 7.08-7.15 (6H, m, Ph), 4.29 (2H, s, CH$_2$), 3.31 (3H, s, CH$_3$).

4-methoxymethylpyrazole: CF$_3$COOH was added to a solution of 1-trityl-4-methoxymethylpyrazole in CH$_2$Cl$_2$/MeOH (1:1). The mixture was heated at 75-80° C. overnight. After cooling to room temperature, the solvent was removed under the vacuum and the residue was applied on the top of a silica-gel column and eluted with methanol/ethyl acetate (5:95). The solvent from the collected fractions was removed under vacuum, and the residue redissolved in ethyl acetate. The title compound was recovered as a slightly yellow oil, after washing the organic phase with a saturated solution of NaHCO$_3$ and distilled water, followed by removal of the solvent and prolonged drying under vacuum. Yield: 38% (60 mg, 0.54 mmol).

$^1$H NMR (CDCl$_3$, δ ppm): 7.57 (2H, s, H-3/5 (pz)), 4.38 (2H, s, CH$_2$), 3.34 (3H, s, CH$_3$).

HC(4-CH$_3$OCH$_2$pz)$_3$ (compound 5): This compound has been synthesized as described in Example 2a for compound 4, starting from 4-methoxymethylpyrazole (60 mg, 0.54 mmol). After purification by gradient HPLC (100% aqueous 0.1% CF$_3$COOH solution→100% CH$_3$CN), using a Nucleosil column (10 μm, 250 mm×4 mm), compound 5 was recovered as a slightly yellow oil. Yield: 16% (10 mg, 0.029 mmol).

$^1$H NMR (CDCl$_3$, δ ppm): 8.24 (1H, s, CH), 7.62 (3H, s, H-3/5 (pz)), 7.54 (3H, s, H-3/5 (pz)), 4.31 (6H, s, 6.9 Hz, CH$_2$) 3.32 (9H, s, OCH$_3$). $^{13}$C NMR (CDCl$_3$, δ ppm): 141.7 (C-3/5(pz)), 128.7 (C-3/5(pz)), 120.1 ((C-4(pz)), 83.3 (CH), 65.1 (CH$_2$), 57.9 (OCH$_3$). FTICR-MS (+) (m/z): 346.2 [M]$^+$ (12).

Tris(4-ethoxymethylpyrazolyl)methane: HC(4-CH$_3$CH$_2$OCH$_2$pz)$_3$ (compound 6)

1-trityl-4-ethoxymethylpyrazole: This compound is a slightly yellow solid and has been obtained as described in 2b for 1-trityl-4-methoxymethylpyrazole, starting from 1-trityl-4-hydroxymethylpyrazole (1.250 g; 3.67 mmol), sodium hydride (221 mg; 5.51 mmol) and iodoethane (1.5 mL; 18.35 mmol), as described in example 2a for 3,5-dimethyl-4-methoxyethyl-1-tritylpyrazole. Yield: 87% (1.174 g, 3.19 mmol).

$^1$H NMR (CDCl$_3$, δ ppm): 7.64 (1H, s, 3-H(pz)), 7.35 (1H, s, 5-H(pz)), 7.26-7.29 (9H, m, Ph), 7.10-7.13 (4H, m, Ph), 4.33 (2H, s, CH$_2$), (2H, q, 7.2 Hz, CH$_2$), 1.18 (3H, t, 7.2 Hz, CH$_3$). $^{13}$C (CDCl$_3$, δ ppm): 143.2 (3/5-C(pz)), 139.9 (C-Ph)), 131.8 (C-Ph), 130.1 (C-Ph), 127.7 (C-Ph), 117.1 (4-C(pz)), 65.4 (CH$_2$), 63.5 (CH$_2$), 15.2 (CH$_3$).

4-ethoxymethylpyrazole: 1-trityl-4-ethoxymethylpyrazole (1.800 g, 4.88 mmol) was dissolved in a mixture of ethanol/acetone (15 ml/5 ml) and 30 mL of 2N HCl was added to the resulting solution. The mixture was heated at 80° C. for 2 h. After cooling to room temperature, the reaction mixture was filtered and washed with dichloromethane. The aqueous layer was basified with 2N NaOH and extracted with dichloromethane. The organic layers were combined, dried over MgSO$_4$ and the solvent was evaporated under vacuum yielding compound 4-ethoxymethylpyrazole as a white oil. Yield: 44% (270 mg, 2.14 mmol).

$^1$H NMR (CDCl$_3$, δ ppm): 7.57 (2H, s, H-3/5 (pz)), 4.43 (2H, s, CH$_2$), 3.50 (2H, q, 6.9 Hz, CH$_2$), 1.20 (3H, t, 6.9 Hz, CH$_3$). $^{13}$C NMR (CDCl$_3$, δ ppm): 133.6 (C-3/5 (pz)), 117.9 (C-4 (pz)), 65.3 (CH$_2$), 63.3 (CH$_2$), 15.1 (CH$_3$).

HC(4-CH$_3$CH$_2$OCH$_2$pz)$_3$ (compound 6): This compound has been obtained as described in Example 2a for compound 4. Starting with 4-ethoxymethylpyrazole (234 mg, 1.86 mmol), and after convenient work-up, a white microcrystalline solid was obtained. Yield: 73% (176 mg, 0.453 mmol).

$^1$H NMR (CDCl$_3$, δ ppm): 8.25 (1H, s, CH), 7.60 (3H, s, H-3/5 (pz)), 7.55 (3H, s, H-3/5 (pz)), 4.32 (6H, s, 6.9 Hz, CH$_2$) 3.45 (6H, q, OCH$_2$), 1.15 (9H, t, CH$_3$). $^{13}$C NMR (CDCl$_3$, δ ppm): 141.6 (C-3/5(pz)), 128.6 (C-3/5(pz)), 120.2 ((C-4 (pz)), 83.15 (CH), 65.6 (CH$_2$), 63.0 (CH$_2$), 15.0 (CH$_3$). FTICR/MS (+) (m/z): 388.2 [M]$^+$ (50%).

Example 3

Production of Chelators of Formula I Having Alkoxy Groups at 3-,5-Positions of the Pyrazolyl Ring Example 3a tris[3,5-(methoxymethyl)pyrazolyl]methane, HC[3,5-(CH$_3$OCH$_2$)$_2$pz]$_3$ (Compound 7) (FIG. 3)

Dimethyl 1-trityl-3,5-pyrazoledicarboxylate: This compound is a white microcrystalline solid that has been isolated following the methodology described in 2b for ethyl-1-tritylpyrazole-4-carboxylate, by reaction of with dimethyl-3,5-pyrazoledicarboxylate (1.411 g, 7.66 mmol) with sodium hydride (250 mg, 10.41 mmol) in dry dimethylformamide (20 mL), followed by treatment with trityl chloride (2.135 g, 7.66 mmol). Yield: 98% (3.200 g, 7.50 mmol).

$^1$H NMR (CDCl$_3$, δ ppm): 7.34 (1H, s, H-4 (pz)), 7.26 (9H, m, Ph), 7.08 (6H, m, Ph), 3.83 (3H, s, CH$_3$), 3.26 (3H, s, CH$_3$).

1-trityl-3,5-bis(hydroxymethyl)pyrazole: To a solution of dimethyl 1-trityl-3,5-pyrazoledicarboxylate (3.200 g, 7.50 mmol) in dry THF (50 mL) were added 30 mL of 1.0 M LiAlH$_4$ in Et$_2$O. The resulting solution was stirred for about 16 h at room temperature (20-25° C.). After this time, the reaction was quenched by the slow addition of 1 mL of distilled water, followed by addition of 1 mL of 10% NaOH and 2.4 mL of water. The solids formed were removed by filtration, and 50 mL of dichloromethane was added to the filtrate. The organic phase was separated, washed with distilled water and a white microcrystalline solid was obtained after evaporation of the solvent under vacuum. Yield: 90% (2.843 g, 6.71 mmol).

$^1$H NMR (CDCl$_3$, δ ppm): 7.28 (914, m, Ph), 7.08 (6H, m, Ph), 6.44 (1H, s, H-4 (pz)), 4.62 (2H, d, CH$_2$), 3.83 (2H, d, CH$_2$), 2.10 (1H, tr, OH), 0.70 (1H, tr, OH).

1-trityl-3,5-bis(methoxymethyl)pyrazole: This compound is a white microcrystalline solid that has been obtained by reacting 1-trityl-3,5-bis(hydroxymethyl)-pyrazole (2.483 g, 6.71 mmol) with sodium hydride (670 mg; 16.8 mmol) and methyl iodide (4.2 mL; 67.5 mmol), as described above in examples 2a and 2b for congener pyrazole derivatives. Yield: 98% (2.606 g, 6.55 mmol).

$^1$H NMR (CDCl$_3$, δ ppm): 7.26 (9H, m, Ph), 7.09 (6H, m, Ph), 6.45 (1H, s, H-4 (pz)), 4.39 (2H, s, CH$_2$), 3.48 (2H, s, CH$_2$), 3.34 (3H, s, CH$_3$), 2.97 (3H, s, CH$_3$).

3,5-bis(methoxymethyl)pyrazole: This compound was obtained by deprotection of trityl-3,5-bis(hydroxymethyl) pyrazole (2.606 g, 6.54 mmol), as described in example 2b for 4-methoxymethylpyrazole. Yield: 58% (589 mg, 3.80 mmol).

$^1$H NMR (CDCl$_3$, δ ppm): 10.72 (1H, br, NH), 6.19 (1H, s, H-4 (pz)), 4.45 (4H, s, CH$_2$), 3.32 (6H, s, CH$_3$). $^{13}$C NMR (CDCl$_3$, δ ppm): 145.2 (C-3/5 (pz)), 103.4 (C-4 (pz)), 66.5 (CH$_2$), 58.0 (CH$_3$).

tris[3,5-(methoxymethyl)pyrazolyl]methane, HC[3,5-(CH$_3$OCH$_2$)$_2$pz]$_3$ (compound 7): To a solution of 3,5-bis (methoxymethyl)pyrazole (331 mg, 2.14 mmol) and [NBu$_4$] Br (35 mg, 0.11 mmol) in distilled water (3 mL) was slowly added Na$_2$CO$_3$ (1.77 g, 2.64 mmol). Then, 1.5 mL of CHCl$_3$ was added and the mixture was heated gently under reflux for 3 days. The organic phase was separated, washed with water and dried over MgSO$_4$. Compound 7 was purified by silica-gel flash chromatography using methanol/dichloromethane (2:98) as eluent. Yield: 34% (116 mg, 0.24 mmol).

Anal. Calcd. for C$_{22}$H$_{34}$N$_6$O$_6$: C, 55.22; H, 7.16; N, 17.56%. Found: C, 55.89; H, 5.49; N, 17.53%.

$^1$H NMR (CDCl$_3$, δ ppm): 8.71 (1H, s, CH), 6.33 (3H, s, H-4 (pz)), 4.38 (6H, s, CH$_2$), 4.30 (6H, s, CH$_2$) 3.31 (9H, s, CH$_3$) 3.18 (9H, s, CH$_3$). $^{13}$C NMR (CDCl$_3$, δ ppm): 149.7 (C-3/5(pz)), 141.1 (C-3/5(pz)), 107.4 (C-4(pz)), 78.7 (C—H), 68.2 (CH$_2$), 64.6 (CH$_2$), 57.9, 57.8 (OCH$_3$). FTICR/MS (+) (m/z): 479.3 [M+H]$^+$ (22%).

Example 3b

Sodium Salt of tris[3,5-(methoxymethyl)pyrazolyl] methane: [{HC[3,5-(CH$_3$OCH$_2$)$_2$pz]$_3$}$_2$Na]I (Compound 8)

Sodium salt of tris[3,5-(methoxymethyl)pyrazolyl] methane, [{HC[3,5-(CH$_3$OCH$_2$)$_2$pz]$_3$}$_2$Na]I (Compound 8)

To a solution of NaI (14 mg, 0.093 mmol) in dry THF (2 mL) was added dropwise a solution of tris[3,5-(methoxymethyl)pyrazolyl]methane (compound 7) (89 mg, 0.186 mmol) in THF. After one hour of reaction at room temperature, the formed white precipitate was separated and vacuum dried. Yield: 68% (70 mg, 0.063 mmol). Elemental analysis. Found (Calcd.) for $C_{44}H_{68}IN_{12}NaO_{12}$: C, 48.35 (47.74); H, 5.97 (6.19); N, 15.34 (15.18);

$^1$H NMR ($D_2O$, δ ppm): 8.55 (1H, s, CH), 6.42 (3H, s, H-4 (pz)), 4.30-4.29 (12H, s, $CH_2$), 3.20 (9H, s, $CH_3$) 3.02 (9H, s, $CH_3$); $^{13}$C NMR ($D_2O$, δ ppm): 152.3 (C-3/5(pz)), 143.4 (C-3/5(pz)), 111.3 (C-4(pz)), 79.3 (C—H), 69.1 ($CH_2$), 65.7 ($CH_2$), 59.7 ($OCH_3$), 59.6 ($OCH_3$). Monocrystals suitable for X-ray structural analysis were obtained by recrystallization of compound 8 from a mixture of acetone/n-hexane.

Example 3c tris[3,5-bis(ethoxymethyl)pyrazolyl]methane, HC[3,5-$(CH_3CH_2OCH_2)_2$pz]$_3$ (Compound 9)

3,5-bis(ethoxymethyl)pyrazole: This compound has been obtained using the same methodologies described in Example 3a for 3,5-bis(methoxymethyl)pyrazole. Yield: 55% (529 mg, 2.87 mmol).

$^1$H NMR ($CDCl_3$, δ ppm): 8.39 (1H, br, NH), 6.20 (1H, s, H-4 (pz)), 4.49 (4H, s, $CH_2$), 3.50 (4H, q, 6.9 Hz, $CH_2$), 1.17 (6H, t, 6.9 Hz, $CH_3$). $^{13}$C NMR ($CDCl_3$, δ ppm): 145.5 (C-3/5(pz)), 103.7 (C-4(pz)), 65.7 ($CH_2$), 64.8 ($CH_2$), 15.0 ($CH_3$).

tris[3,5-bis(ethoxymethyl)pyrazolyl]methane, HC[3,5-$(CH_3CH_2OCH_2)_2$pz]$_3$ (Compound 9): Compound 9 has been prepared using the same methodology described for compound 7. Starting from 3,5-bis(ethoxymethyl)pyrazolyl (485 mg, 2.63 mmol) a slightly yellow oil was obtained, after the appropriate work-up. Yield: 47% (230 mg, 0.41 mmol).

$^1$H NMR ($CDCl_3$, δ ppm): 8.68 (1H, s, CH), 6.32 (3H, s, H-4 (pz)), 4.41 (6H, s, $CH_2$), 4.32 (6H, s, $CH_2$) 3.46 (6H, q, 6.9 Hz, $CH_2$) 3.34 (6H, q, 6.9 Hz, $CH_2$), 1.16 (9H, t, 6.9 Hz, $CH_3$), 1.06 (9H, t, 6.9 Hz, $CH_3$). $^{13}$C NMR ($CDCl_3$, δ ppm): 150.0 (C-3/5(pz)), 141.7 (C-3/5(pz)), 107.2 (C-4(pz)), 79.0 (C—H), 66.4 ($CH_2$), 65.8 ($CH_2$), 65.5 ($CH_2$), 62.9 ($CH_2$), 15.1, ($CH_3$), 14.9 ($CH_3$). FTICR/MS (+) (m/z): 563.4 $[M+H]^+$ (46%).

Example 4

Production of a chelator of formula I having alkoxy groups at the 3-, 4- and 5-positions of the pyrazolyl ring: tris[3,4,5-tris(methoxymethyl)pyrazolyl]methane, HC[3,4,5-$(CH_3OCH_2)_3$pz]$_3$ (compound 10) (FIG. 5).

Trimethyl-3,4,5-pyrazoletricarboxylate: 3,4,5-Pyrazoletricarboxylic acid (D. Chambers, W. A. Denny, J. Org. Chem., 1985, 50, 4736-4738) (2.15 g, 10.7 mmol) was dissolved in methanol (80 mL) and concentrated $H_2SO_4$ (0.85 mL) was added. After overnight reflux, the solvent was evaporated in the rotary evaporator. The residue was dissolved in water (80 mL) and the product extracted with $CHCl_3$ (4×80 mL). The organic phase was dried over $MgSO_4$, separated and the solvent evaporated under vacuum. The crude product was purified by silica-gel chromatography using gradient elution, from 100% $CHCl_3$ to 100% MeOH. The collected fractions were evaporated under vacuum and the white solid analysed. Yield: 32% (830 mg, mmol).

$^1$H NMR ($CDCl_3$, δ ppm): 3.95 (3H, s, $COOCH_3$), 3.93 (6H, s, $COOCH_3$).

Trimethyl 1-trityl-3,4,5-pyrazoletricarboxylate: The synthesis of this compound was done by tritylation of trimethyl-3,4,5-pyrazoletricarboxylate (1680 mg, 6.94 mmol) using a procedure similar to the one described in examples 2 and 3 for the synthesis of other tritylated pyrazole derivatives. The starting pyrazole reacted with sodium hydride (405 mg, 10.13 mmol) in dry dimethylformamide (80 mL) for 30 min at room temperature. Then, trityl chloride (1935 mg, 6.94 mmol) was added and the reaction mixture stirred overnight at room temperature. After removal of the solvent under vacuum, the resulting residue was washed with distilled water, n-hexane, and finally dried under vacuum to afford the title compound, as a white microcrystalline solid. Yield: 90% (3.034 g, 6.26 mmol).

$^1$H NMR ($CDCl_3$, δ ppm): 7.30-7.24 (9H, m, Ph), 7.13-7.09 (6H, m, Ph), 3.84 (3H, s, $COOCH_3$), 3.80 (3H, s, $COOCH_3$), 3.19 (3H, s, $COOCH_3$).

1-trityl-3,4,5-tris(hydroxymethyl)pyrazole: To a solution of trimethyl 1-trityl-3,4,5-pyrazoletricarboxylate (3.034 g, 6.26 mmol) in dry THF (60 mL) were added 50 mL of 1.0 M $LiAlH_4$ in $Et_2O$. The resulting solution was stirred for about 16 h at room temperature (20-25° C.). After this time, the reaction was quenched by the slow addition of 1.5 mL of distilled water, followed by addition of 1.5 mL of 10% NaOH and 3.5 mL of water. The solids formed were removed by filtration, and 80 mL of dichloromethane was added to the filtrate. The organic phase was separated, washed with distilled water (70 mL) and, after separation from the aqueous phase, was dried over $MgSO_4$. After separation of the organic phase, the solvent was evaporated under vacuum yielding a yellowish solid. Yield: 73% (1.823 g, 4.54 mmol).

$^1$H NMR ($CDCl_3$, δ ppm): 7.29 (9H, m, Ph), 7.08 (6H, m, Ph), 4.67 (2H, d, $CH_2$), 4.63 (2H, d, $CH_2$), 4.05 (2H, d, $CH_2$), 2.68 (1H, tr, OH), 2.41 (1H, tr, OH), 0.84 (1H, tr, OH).

1-trityl-3,4,5-tris(methoxymethyl)pyrazole: To a solution of 1-trityl-3,4,5-tris(hydroxymethyl)-pyrazole (1.823 g, 4.54 mmol) in dry THF (60 mL) was added 685 mg of a 60% NaH suspension (28.5 mmol), and the mixture was stirred for 4 h at room temperature (20-25° C.). After this time, 4.35 mL of methyl iodide (mmol) was added and the mixture was allowed to react for 2 h. The solvent was removed under vacuum and the residue redissolved in dichloromethane (100 mL) and the organic phase was washed with distilled water. The organic phase was separated, dried over $MgSO_4$ and the filtrate was vacuum dried. The white microcrystalline solid was formulated as the above mentioned compound based on NMR analysis. Yield: 98% (2.12 g, mmol).

$^1$H NMR ($CDCl_3$, δ ppm): 7.26 (9H, m, Ph), 7.12 (6H, m, Ph), 4.44 (4H, d, $CH_2$), 3.78 (2H, s, $CH_2$), 3.32 (3H, s, $CH_3$), 3.31 (3H, s, $CH_3$), 2.77 (3H, s, $CH_3$).

3,4,5-tris(methoxymethyl)pyrazole: This compound is a white microcrystalline solid obtained by deprotection of 1-trityl-3,4,5-tris(methoxymethyl)pyrazole (2.125 g, 4.80 mmol), as described in example 2b for 4-methoxymethylpyrazole. Yield: 78% (752 mg, 3.75 mmol).

$^1$H NMR ($CDCl_3$, δ ppm): 10.85 (1H, br, NH), 4.51 (4H, s, $CH_2$), 4.37 (2H, s, $CH_2$), 3.35 (6H, s, $CH_3$) 3.29 (3H, s, $CH_3$). $^{13}$C NMR ($CDCl_3$, δ ppm): 144.1 (C-3/5 (pz)), 113.7 (C-4 (pz)), 65.5 ($CH_2$), 63.7 ($CH_2$), 58.1 ($CH_3$), 57.7 ($CH_3$).

tris[3,4,5-(methoxymethyl)pyrazolyl]methane, HC[3,4,5-$(CH_3OCH_2)_3$pz]$_3$ (compound 10). To a solution of 3,4,5-tris(methoxymethyl)pyrazole (202 mg, 1.01 mmol) and [$NBu_4$]Br (16.8 mg, 1.01 mmol) in distilled water (1.5 mL) was slowly added $Na_2CO_3$ (660 mg, mmol). Then, 0.8 mL of $CHCl_3$ was added and the mixture was heated gently under reflux for 5 days. The organic phase was separated, washed with water and dried over $MgSO_4$. Compound was purified by silica-gel flash chromatography using methanol/dichloromethane (2:98) as eluent. Yield: 34% (116 mg, 0.24 mmol).

$^1$H NMR ($CDCl_3$, δ ppm): 8.83 (1H, s, CH), 4.42 (611, s, $CH_2$), 4.38 (6H, s, $CH_2$), 4.37 (6H, s, $CH_2$) 3.25 (18H, s, $CH_3$)

3.13 (9H, s, CH$_3$)). $^{13}$C NMR (CDCl$_3$, δ ppm): 148.5 (C-3/5 (pz)), 139.6 ($\overline{C}$-3/5 (pz)), 117.9 (C-4 (pz)), 78.7 (CH), 67.1 (CH$_2$), 63.6 (CH$_2$), 57.8 (CH$_3$), 57.5 (CH$_3$).

Example 5

Production of a Chelator of Class II Having an Alkoxy Group at the Primary Amine

Example 5a

N-(2-methoxyethyl)-2,2-di(1H-pyrazol-1-yl)ethanamine: MeO(CH$_2$)$_2$NHCH$_2$CH(pz)$_2$ (Compound 11) (FIG. 6)

To a solution of 2,2'-bis(pyrazolyl)ethanamine (327 mg, 1.8 mmol) in dry ethanol (15 mL) was added excess of 1-chloro-2-methoxyethane (526 μL; 5.8 mmol), K$_2$CO$_3$ (1.281 g, 9.2 mmol) and KI (30 mg, 0.18 mmol), and the mixture refluxed for 4 days. After this time, the solvent was removed under vacuum and the residue was applied on a silica gel column which was eluted with MeOH/CHCl$_3$ (5:95). Removal of the solvent from the collected fractions yielded the title compound in the form of a brown oil. Yield: 21% (89 mg, 0.38 mmol).

$^1$H NMR (CDCl$_3$): δ$_H$ (d, H-3/5 (pz), 2H), 7.53 (d, H-3/5 (pz), 2H), 6.51 (t, CH, 1H), 6.25 (t, H-4 (pz), 2H), 3.69 (d, —NHCH$_2$CH, 2H), $\overline{3}$.41 (t, OCH$_2$, 2H), 3.28 (s, —OCH$_3$, 3H), 2.2$\overline{7}$ (t, NCH$_2$CH$_2$, 2H). $^{13}\overline{C}$ NMR (CDCl$_3$): δ$_C$ 14$\overline{0}$.3 (C-3 (pz)), 128.9 ($\overline{C}$-5 (pz)), 106.6 (C-4 (pz)), 75.0 (CH), 71.8 (CH$_2$), 58.8 (CH$_3$O), 51.6 (CH$_2$), 48.7 (CH$_2$). FT/ICR-MS ($\overline{+}$) (m/z): 236.$\overline{2}$ [M+H]$^+$ (10%).

Example 6

Production of a Chelator of Class III Having Ether Groups at the Secondary Amine and/or at the 3- and 5-Position of the Pyrazolyl Rings

Example 6a bis(2-(3,5-bis(methoxymethyl)-1H-pyrazol-1-yl) ethyl)amine: {3,5-(CH$_3$OCH$_2$)$_2$}pz(CH$_2$)$_2$NH(CH$_2$)$_2${3,5-(CH$_2$OCH$_3$)$_2$ pz)} (Compound 12) (FIG. 7)

A suspension of NaH (0,240 g, 10 mmol) in dry DMF (20 mL) was slowly added to 3,5-bis(methoxymethyl)pyrazole (500 mg; 3.42 mmol) in dry DMF (10 mL). The reaction mixture was left at room temperature for 4 h. A solution of bis-(2-chloroethyl)amine hydrochloride (305 mg, 1.71 mmol) was then slowly added, and the mixture reacted at room temperature for 5 days. The solvent was evaporated and the crude compound was purified by silica gel chromatography (eluent: CHCl$_3$/MeOH (95:5)). The collected fractions were vacuum dried affording compound 12 as slightly yellow oil Yield: 40% (261 mg; 0.68 mmol).

$^1$H NMR (300 MHz, CDCl$_3$, δ (ppm)): 6.18 (s, H-4 (pz), 2H), 4.39 (d, —CH$_2$, 8H), 4.14 (t, —CH$_2$, 4H), 3.35 (s, —OCH$_3$, 6H), 3.28 (s, —OCH$_3$, 6H), 3.00 (t, —CH$_2$, 4H);

$^{13}$C NMR (75.37 MHz, CDCl$_3$, δ (ppm)) 148.3, 139.4, 106.1, 68., 64.3, 57.9, 57.6, 49.0, 48.9.

Example 6b

2-(3,5-bis(methoxymethyl)-1H-pyrazol-1-yl)-N-(2-(3,5-bis(methoxymethyl)-1H-pyrazol-1-yl)ethyl)-N-(2-methoxyethyl)ethanamine: {3,5-(CH$_3$OCH$_2$)$_2$}pz (CH$_2$)$_2$N((CH$_2$)$_2$OMe)(CH$_2$)$_2${3,5-(CH$_2$OCH$_3$)$_2$ pz)} (Compound 13) (FIG. 7)

Ethyl 2-(bis(2-(3,5-bis(methoxymethyl)-1H-pyrazol-1-yl) ethyl)amino)acetate. To a solution of compound 12 (0,261 g, 0.68 mmol) in acetonitrile (15 mL) was added potassium carbonate (193 mg, 1.4 mmol) and potassium iodide (6 mg, 0.03.4 mmol). To this suspension was then added ethyl bromo acetate (155 μL, 1.4 mmol). The reaction mixture was refluxed overnight, under nitrogen. The supernatant was separated and the solvent evaporated under vacuum. The orange solid obtained was analysed. Yield: (280 mg; 0.6 mmol).

$^1$H NMR (300 MHz, CDCl$_3$, δ (ppm)): 6.15 (s, H-4 (pz), 2H), 4.39 (d, —CH$_2$, 8H), 4.13-4.06 (q, —CH$_2$, 8H), 4.01 (t, —CH$_2$, 4H), 3.37-3.28 (m, —OCH$_3$+—CH$_2$, 12+2H), 3.07 (t, —CH$_2$, 4H), 1.21 (t, —CH$_3$, 3H).

2-(bis(2-(3,5-bis(methoxymethyl)-1H-pyrazol-1-yl)ethyl) amino)ethanol: This compound has been obtained by reacting a solution of ethyl 2-(bis(2-(3,5-bis(methoxymethyl)-1H-pyrazol-1-yl)ethyl)amino)acetate (280 mg; 0.6 mmol) in dry THF (10 mL) with LiAlH$_4$. The title compound was isolated following the same methodology above described for the synthesis of other (hydroxymethyl)pyrazoles (see example 6). Yield: 60% (170 mg, 0.4 mmol).

$^1$H NMR (300 MHz, CDCl$_3$, δ (ppm)): 6.18 (s, H-4 (pz), 2H), 4.38-4.34 (m, —CH$_2$, 4H), 3.99 (t, —CH$_2$, 4H), 3.49 (m, —CH$_2$, 2H), 3.34 (s, —OCH$_3$, 6H), 3.30 (s, —OCH$_3$, 6H), 2.92 (t, —CH$_2$, 4H), 2.67 (t, —CH$_2$, 2H).

{3,5-(CH$_3$OCH$_2$)$_2$}pz(CH$_2$)$_2$N((CH$_2$)$_2$OMe)(CH$_2$)$_2${3,5-(CH$_2$OCH$_3$)$_2$pz)} (compound 13): Compound 13 has been obtained by reacting a solution of 2-(bis(2-(3,5-bis(methoxymethyl)-1H-pyrazol-1-yl)ethyl)amino)ethanol (170 mg, 0.4 mmol) in dry THF (10 mL) with NaH and CH$_3$I. Yield: 30% (46 mg; 0.12 mmol).

$^1$H NMR (CDCl$_3$): δ$_H$ 6.17 (s, H-4 (pz), 2H, 4.40-4.34 (m, —CH$_2$, 8H), 4.07-3.95 (m, —CH$_2$, 4H), 3.35-3.23 (m, —OCH$_3$+—CH$_2$, 15+2H), 3.21-2.89 (m, —CH$_2$, 4H), 2.73-2.69 (m, —CH$_2$, 2H).

Example 7

Production of Tricarbonyl Rhenium Complexes with Chelators of General Formulae (I), (II) or (III)

Although the preferred complexes according to this invention, in that they are useful for diagnosis, are the $^{99m}$Tc complexes, the Re complexes are used as a model to characterise them, as the $^{99m}$Tc complexes are not available in sufficient quantities to be characterised by the normal analytical techniques, such as NMR. After the Re complexes have been thus characterised, HPLC is performed on both the Re complexes and the corresponding $^{99m}$Tc complexes to determine if the retention time is the same for both.

The synthesis of the Re complexes was done by reaction of the chelators of general formula (I), (II) or (III) with common Re(I) starting materials, such as (NEt$_4$)$_2$[Re(CO)$_3$Br$_3$] or [Re (CO)$_3$(H$_2$O)$_3$]Br (FIG. 8). In all the complexes the chelators act as neutral and tridentate, as confirmed by $^1$H and $^{13}$C NMR spectroscopy (FIGS. 9 and 10) and by X-ray diffraction analysis (FIG. 11).

Example 7a

Tricarbonyl Rhenium Complex of O-methyl-1,1,1-tris(pyrazolyl)ethanol (Compound 1): [Re(CO)$_3$ {CH$_3$OCH$_2$C(pz)$_3$}] (Compound 14)

A solution of (NEt$_4$)$_2$[Re(CO)$_3$Br$_3$] (80 mg, 0.104 mmol) and compound 1 (27 mg, 0.104 mmol) in ethanol (15 mL) was heated under reflux for about 16 h. The solvent was removed under vacuum and the residue extracted with THF. Compound 14 was recovered as a beige solid, after removal of THF, washing with toluene and drying under vacuum. Yield: 71% (45 mg, 0.074 mmol).

Analysis calculated for C$_{15}$H$_{14}$N$_6$O$_4$BrRe: C, 29.61%; H, 2.32%; N, 13.81%. Found: C, 28.27%; H, 2.48%; N, 11.23%. IR Data (1(KBr, v/cm$^{-1}$): 1914 (vs) and 2042 (s) (C≡O).
$^1$H NMR (CDCl$_3$, $\delta_H$ ppm): 8.98 (1H, br, H-3/5 (pz)), 8.49 (2H, br, H-3/5 (pz)), 8.01 (3H, br, H-3/5 (pz)), 6.58 (3H, br, H-4 (pz)), 6.12 (2H, s, CH$_2$), 4.06 (3H, s, CH$_3$). $^{13}$C NMR (CDCl$_3$, $\delta_C$ ppm): 193.8 (br, CO), 147.2 (C-3/5 (pz)), 135.8 (C-3/5 (pz)), 134.6 (C-3/5 (pz)), 109.9 (C-4 (pz)), 109.0 (C-4 (pz)), 85.2 (Cpz$_3$), 70.4 (CH$_2$), 60.7 (CH$_3$).

Example 7b

Tricarbonyl Rhenium Complex of O-ethyl-1,1,1-tris(pyrazolyl)ethanol (Compound 2): [Re(CO)$_3$ {CH$_3$CH$_2$OCH$_2$C(pz)$_3$}] (Compound 15)

Complex 15 was synthesized as above described for compound 14 by reaction of (NEt$_4$)$_2$[Re(CO)$_3$Br$_3$] with CH$_3$CH$_2$OCH$_2$C(pz)$_3$ (2). However, compound 15 was always obtained slightly contaminated with [NEt$_4$]Br, due to their similar solubilities in the most common solvents.

IR Data (KBr, v/cm$^{-1}$): 1926 (s), 1946 (s) and 2042 (s) (C≡O).
$^1$H NMR (CDCl$_3$, $\delta$ ppm): 9.22 (1H, br, H-3/5 (pz)), 8.49 (2H, d, H-3/5 (pz)), 8.02 (2H, br, H-3/5 (pz)), 7.98 (1H, br, H-3/5 (pz)), 6.58 (3H, tr, H-4 (pz)), 6.27 (2H, s, CH$_2$), 4.38 (2H, q, CH$_2$), 1.37 (3H, tr, CH$_3$).

Example 7c

Tricarbonyl Rhenium Complex of O-n-propyl-1,1,1-tris(pyrazolyl)ethanol (Compound 3): [Re(CO)$_3$ {CH$_3$CH$_2$CH$_2$OCH$_2$C(pz)$_3$}] (Compound 16)

A solution of (NEt$_4$)$_2$[Re(CO)$_3$Br$_3$] (100 mg, 0.13 mmol) and compound 3 (40 mg, 0.14 mmol) in ethanol (15 mL) was heated under reflux for about 16 h. The solvent was evaporated under vacuum and the residue was washed with THF and water. The insoluble solid was dried under vacuum and formulated as compound 16. Yield: 30% (25 mg, 0.039 mmol).

Analysis calculated for C$_{17}$H$_{18}$N$_6$O$_4$BrRe: C, 32.08%; H, 2.85%; N, 13.20%. Found: C, 31.39%; H, 2.41%; N, 12.72%. IR Data (KBr, v/cm$^{-1}$): 1940 (vs) and 2042 (s) (C≡O).
$^1$H NMR (CDCl$_3$, $\delta$ ppm): 9.20 (1H, br, H-3/5 (pz)), 8.39 (2H, br, H-3/5 (pz)), 8.04 (2H, br, H-3/5 (pz)), 7.99 (1H, br, H-3/5 (pz)), 6.58 (3H, br, H-4 (pz)), 6.25 (2H, br, CH$_2$), 4.27 (2H, br, CH$_2$), 1.75 (2H, br, CH$_2$), 0.98 (3H, br, CH$_3$).

Example 7d

Tricarbonyl Rhenium Complex of tris[3,5-(methoxymethyl)pyrazolyl]methane (Compound 7): [Re(CO)$_3$ {HC[3,5-(CH$_3$OCH$_2$)$_2$pz]$_3$}] (Compound 17)

Complex 17 was obtained by reacting (NEt$_4$)$_2$[Re(CO)$_3$(H$_2$O)$_3$]Br with HC[3,5-(CH$_3$OCH$_2$)$_2$pz]$_3$ (compound 7) in ethanol under reflux for about 16 h. IR and $^1$H NMR analyses of the crude product, after removal of the solvent under vacuum, have shown the formation of the desired compound.

IR Data (KBr, v/cm$^{-1}$): 1945 (vs) and 2037 (s) (C≡O).
$^1$H NMR (CDCl$_3$, $\delta$ ppm): 9.47 (1H, s, CH), 6.70 (3H, s, H-4 (pz)), 4.96 (6H, s, CH$_2$), 4.63 (6H, s, CH$_2$) 3.55 (9H, s, CH$_3$) 3.50 (9H, s, CH$_3$).

Example 8

Production of Tricarbonyl $^{99m}$Tc Complexes with Chelators of General Formula (I) (FIG. 12)

In a nitrogen-purged glass vial, 100 μL of a 10$^{-3}$10$^{-2}$ M aqueous solution of compounds 1-3, 7, and of the already described ligands HC(pz)$_3$ and HC(3,5-Me$_2$pz)$_3$ were added to 900 μL (5-15 mCi) of the organometallic precursor fac-[$^{99m}$Tc(OH$_2$)$_3$(CO)$_3$]$^+$, and the mixture was heated at 70-100° C. for 30-60 min. After this time, complexes 14a-18a, 23a and 24a have been obtained in >90% yield, as checked by gradient HPLC analysis (100% aqueous 0.1% CF$_3$COOH solution→100% CH$_3$CN (or 100% CH$_3$OH)) using a Nucleosil column (10 μm, 250 mm×4 mm). The chemical identity of the $^{99m}$Tc complexes was confirmed by comparing their HPLC chromatograms with the HPLC profile of the analogue Re complexes (FIG. 13). The characterization of the $^{99m}$Tc complexes comprised also the determination of the octanol-water partition coefficient (log P$_{o/w}$) values by the multiple back extraction method under physiological conditions (n-octanol/0.1 M PBS, pH 7.4). The retention time and log P$_{o/w}$ values obtained for complexes 14a-18a, 23a and 24a are given in Table 1.

TABLE 1

HPLC retention time (t$_R$) and log P$_{o/w}$ values for complexes 6a-11a

| Complex | t$_R$(min) | log P$_{o/w}$ |
|---|---|---|
| 14a | 20.6 | 0.32 |
| 15a | 21.7 | 0.68 |
| 16a | 20.8 | 1.18 |
| 17a | 20.1 | 0.58 |
| 18a | 20.8 | 0.64 |
| 23a | 19.6 | 1.2 |
| 24a | 16.6 | 0.55 |

Example 9

Biodistribution of the $^{99m}$Tc Complexes with Chelators of General Formula (I)

These studies have been designed as a preliminary screening tool to evaluate the biological profile of the cationic tricarbonyl complexes. The biodistribution of the complexes was evaluated in groups of 5 female CD-1 mice (randomly bred, Charles River) weighing approximately 20-25 g each and have been performed according to EEC Legislation (National Law 129/92) on ethical and animal care. Animals were intravenously injected with 100 μL (1.5-8.0 MBq) of each preparation via the tail vein and were maintained on normal diet ad libitum. Mice were killed by cervical dislocation at 1 h and 2 h p.i. The injected radioactive dose and the radioactivity remaining in the animal after sacrifice were measured in a dose calibrator (Aloka, Curiemeter IGC-3, Tokyo, Japan). The difference between the radioactivity in the injected and sacrificed animal was assumed to be due to total excretion from whole body animal. Blood samples were taken by cardiac puncture at sacrifice. Tissue samples of the main organs were then removed, weighted and counted in a gamma counter (Berthold). Biodistribution results were expressed as percentage of the injected dose per organ (% ID/organ) and/or per gram tissue (% ID/g). For blood, total activity was calculated assuming that this organ constitutes 6% of the total weight, respectively. The remaining activity in the carcass was also measured in a dose calibrator. Biodistribution data for some $^{99m}$Tc complexes are shown in Tables 2 and 3. Table 4 also shows a direct comparison of biodistribution and relevant ratios for complexes 17a and 18a and the heart imaging agent $^{99m}$Tc-Sestamibi in the same animal model (% ID/g of wet organ).

TABLE 2

Biodistribution data for complexes 14a-18a, 23a, 24a (% ID/g of wet organ).

| Organ | (23a) 1 h | (23a) 2 h | (24a) 1 h | (24a) 2 h | (14a) 1 h | (14a) 2 h | (15a) 1 h | (15a) 2 h |
|---|---|---|---|---|---|---|---|---|
| Blood | 1.4 ± 0.1 | 1.3 ± 0.2 | 5.4 ± 1.2 | 1.6 ± 0.3 | 1.5 ± 0.1 | 0.8 ± 0.1 | 0.5 ± 0.2 | 0.3 ± 0.1 |
| Liver | 18.7 ± 4.7 | 19.1 ± 5.3 | 9.9 ± 2.7 | 4.9 ± 1.3 | 6.9 ± 2.3 | 6.2 ± 2.1 | 3.8 ± 2.0 | 1.6 ± 0.6 |
| Heart | 4.1 ± 0.7 | 4.3 ± 1.8 | 1.9 ± 0.3 | 1.4 ± 0.3 | 1.3 ± 0.3 | 0.9 ± 0.2 | 3.6 ± 0.5 | 1.8 ± 0.7 |
| Lung | 3.2 ± 0.3 | 2.1 ± 0.7 | 1.4 ± 0.3 | 1.2 ± 0.2 | 0.8 ± 0.2 | 0.8 ± 0.3 | 0.9 ± 0.1 | 0.6 ± 0.3 |
| Kidney | 44.7 ± 5.1 | 40.0 ± 5.2 | 7.2 ± 0.5 | 3.9 ± 0.8 | 3.3 ± 0.9 | 2.7 ± 0.4 | 5.0 ± 1.4 | 2.8 ± 0.5 |

| Organ | (16a) 1 h | (16a) 2 h | (17a) 1 h | (17a) 2 h | (18a) 1 h | (18a) 2 h |
|---|---|---|---|---|---|---|
| Blood | 0.36 ± 0.06 | 0.22 ± 0.06 | 0.9 ± 0.1 | 0.9 ± 0.2 | 0.52 ± 0.09 | 0.34 ± 0.02 |
| Liver | 4.3 ± 1.6 | 2.1 ± 0.5 | 8.7 ± 1.8 | 5.3 ± 0.9 | 5.1 ± 0.9 | 5.0 ± 2.4 |
| Heart | 1.8 ± 0.4 | 0.4 ± 0.2 | 10.1 ± 3.1 | 9.9 ± 3.1 | 18.2 ± 3.2 | 15.8 ± 2.1 |
| Lung | 0.9 ± 0.5 | 0.29 ± 0.04 | 3.1 ± 0.8 | 2.3 ± 0.8 | 4.3 ± 1.3 | 2.2 ± 0.3 |
| Kidney | 8.6 ± 2.1 | 7.8 ± 3.0 | 25.0 ± 3.3 | 14.7 ± 1.8 | 16.1 ± 2.3 | 9.9 ± 0.9 |

TABLE 3

Heart/Blood, Heart/Liver and Heart/Lung ratios for complexes 14a-18a, 23a and 24a.

| Ratios | (23a) 1 h | (23a) 2 h | (24a) 1 h | (24a) 2 h | (14a) 1 h | (14a) 2 h | (15a) 1 h | (15a) 2 h |
|---|---|---|---|---|---|---|---|---|
| Heart/Blood | 2.6 ± 0.3 | 3.8 ± 0.1 | 0.34 ± 0.06 | 0.9 ± 0.2 | 0.9 ± 0.1 | 1.1 ± 0.1 | 8.2 ± 2.9 | 9.6 ± 0.6 |
| Heart/Liver | 0.22 ± 0.03 | 0.25 ± 0.07 | 0.20 ± 0.04 | 0.29 ± 0.05 | 0.18 ± 0.03 | 0.3 ± 0.1 | 1.4 ± 0.9 | 1.3 ± 0.7 |
| Heart/Lung | 1.3 ± 0.1 | 2.0 ± 0.3 | 1.3 ± 0.3 | 1.2 ± 0.3 | 1.7 ± 0.3 | 1.6 ± 0.4 | 4.0 ± 0.7 | 4.3 ± 1.4 |

| Ratios | (16a) 1 h | (16a) 2 h | (17a) 1 h | (17a) 2 h | (18a) 1 h | (18a) 2 h |
|---|---|---|---|---|---|---|
| Heart/Blood | 4.6 ± 0.9 | 1.6 ± 0.5 | 11.2 ± 3.5 | 11.5 ± 2.2 | 35.0 ± 5.3 | 47.3 ± 2.3 |
| Heart/Liver | 0.5 ± 0.2 | 0.15 ± 0.05 | 1.1 ± 0.2 | 1.6 ± 0.5 | 3.5 ± 0.9 | 3.5 ± 0.9 |
| Heart/Lung | 2.2 ± 0.8 | | 3.3 ± 0.4 | 4.6 ± 1.8 | 4.9 ± 1.1 | 7.0 ± 0.6 |

TABLE 4

Biodistribution data and relevant ratios for complexes 17a and 18a and the heart imaging agent $^{99m}$Tc-Sestamibi (% ID/g of wet organ).

| | (17a) | | | (18a) | | | $^{99m}$Tc-Sestamibi | | |
|---|---|---|---|---|---|---|---|---|---|
| | 5 min | 60 min | 120 min | 5 min | 60 min | 120 min | 5 min | 60 min | 120 min |
| Organ | | | | | | | | | |
| Blood | | 0.9 ± 0.1 | 0.9 ± 0.2 | 1.14 ± 0.09 | 0.52 ± 0.09 | 0.34 ± 0.02 | 2.0 ± 0.4 | 1.2 ± 0.4 | 1.1 ± 0.3 |
| Liver | | 8.7 ± 1.8 | 5.3 ± 0.9 | 9.2 ± 0.9 | 5.1 ± 0.9 | 5.0 ± 2.4 | 9.0 ± 1.8 | 5.6 ± 0.3 | 5.0 ± 2.1 |
| Heart | | 10.1 ± 3.1 | 9.9 ± 3.1 | 15.8 ± 1.7 | 18.2 ± 3.2 | 15.8 ± 2.1 | 9.4 ± 0.4 | 8.0 ± 0.6 | 7.9 ± 1.0 |

TABLE 4-continued

Biodistribution data and relevant ratios for complexes 17a and 18a and the heart imaging agent $^{99m}$Tc-Sestamibi (% ID/g of wet organ).

|  | (17a) | | | (18a) | | | $^{99m}$Tc-Sestamibi | | |
|---|---|---|---|---|---|---|---|---|---|
|  | 5 min | 60 min | 120 min | 5 min | 60 min | 120 min | 5 min | 60 min | 120 min |
| Lung | | 3.1 ± 0.8 | 2.3 ± 0.8 | 4.2 ± 0.5 | 4.3 ± 1.3 | 2.2 ± 0.3 | 2.4 ± 0.6 | 1.3 ± 0.2 | 0.9 ± 0.2 |
| Kidney | | 25.0 ± 3.3 | 14.7 ± 1.8 | 43.4 ± 4.3 | 16.1 ± 2.3 | 9.9 ± 0.9 | 34.2 ± 2.4 | 14.8 ± 6.1 | 9.7 ± 1.8 |
| Ratios | | | | | | | | | |
| Heart/Blood | | 11.2 ± 3.5 | 11.5 ± 2.2 | 13.9 ± 1.2 | 35.0 ± 5.3 | 47.3 ± 2.3 | 4.1 ± 0.7 | 7.9 ± 3.6 | 7.4 ± 2.3 |
| Heart/Liver | | 1.1 ± 0.2 | 1.6 ± 0.5 | 1.7 ± 0.3 | 3.5 ± 0.9 | 3.5 ± 0.9 | 0.9 ± 0.2 | 1.4 ± 0.1 | 1.8 ± 0.7 |
| Heart/Lung | | 3.3 ± 0.4 | 4.6 ± 1.8 | 3.8 ± 0.4 | 4.9 ± 1.1 | 7.0 ± 0.6 | 3.5 ± 0.8 | 6.3 ± 0.6 | 9.2 ± 1.1 |

The invention claimed is:

1. Tridentate chelators of the type tris(pyrazolyl)methane ($R_1C(pf^*)_3$) and bis(pyrazolyl)amine($(pz^*)_2CH(CH_2)_n$NHR$_1$ or $(pz^*)(CH_2)_nNR_1(CH_2)_n(pz^*)$) of formulae (I), (II) and (III) respectively:

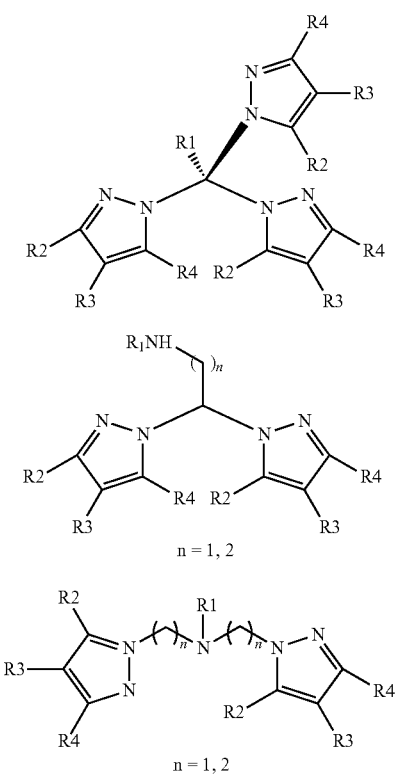

wherein at least one of $R_1$, $R_2$, $R_3$ and $R_4$ is a linear or macrocyclic ether group of the type —$R^x$—O—$R^Y$ or $[(CH_2)_xO]_y(CH_2)_z$ (x=2-3, y=3-8, z=2-5), respectively, and each of the other three R groups is independently hydrogen; a linear or branched, saturated or unsaturated $C_1$ to $C_9$ alkyl; a saturated or unsaturated carbocyclic group; a saturated or unsaturated heterocyclic or heteroaliphatic group with one or more atoms selected from O, N and S, wherein said carbocyclics, heterocyclics and heteroaliphatics are optionally substituted by one or more linear or branched, saturated or unsaturated $C_1$ to $C_9$ alkyls; an ether group —$R^x$—O—$R^Y$ or $[(CH_2)_xO]_y(CH_2)_z$ (x=2-3, y=3-8, z=2-5), wherein $R^x$ and $R^Y$ are independently linear or branched, saturated or unsaturated $C_1$ to $C_9$ alkyl, or saturated or unsaturated carbocyclics, any of which alkyl and/or carbocyclic groups may be substituted or unsubstituted, provided that when the tridentate chelator is of the type of formula (I), when $R_1$ is —$R^x$—O—$R^Y$ wherein $R^Y$ is substituted, and $R_2$, $R_3$, and $R_4$ are each H, $R^Y$ is not substituted apically by a further tris(pyrazolyl)methane moiety;

and when $R_1$ is —$R^x$—O—$R^Y$ and $R_2$, $R_3$ and $R_4$ are each H, $R_1$ cannot be —$CH_2$—O—$CH_2$-(p-$^t$Bu-$C_6H_4$).

2. Tridentate chelators according to claim 1, wherein the chelators are selected from those represented by formula (I).

3. Tridentate chelators according to claim 1, wherein the chelators are selected from those represented by formula (II).

4. Tridentate chelators according to claim 1, wherein the chelators are selected from those represented by formula (III).

5. Tridentate chelators according to claim 1, wherein in each of Formulae (I), (II) and (III), at least one of the $R_1$, $R_2$, $R_3$, $R_4$ is a linear ether group of the type —$R^x$—O—$R^Y$.

6. Tridentate chelators according to claim 1, wherein in each of Formulae (I), (II) and at least one of the $R_1$, $R_2$, $R_3$, $R_4$ is a macrocyclic ether group of the type $[(CH_2)_xO]_y(CH_2)_z$ (x=2-3, y=3-8, z=2-5).

7. A process for the preparation of tridentate chelators of formulae (I), (II) and (III), comprising contacting a compound of the formula

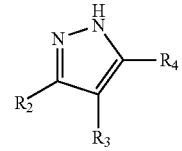

with a compound selected from a trihalomethane, a compound of the formula

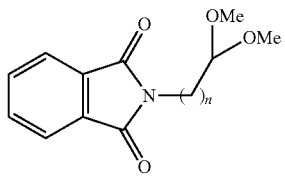

or a compound of the formula Hal-$(CH_2)_n$—$NR^1$—$(CH_2)_n$-Hal (wherein Hal=a halogen), and reacting a subsequent product with an alkyl halide, aryl halide, or a halide substituted ether compound, wherein each of at least one R1, R2, R3 and R4 is a linear or macrocyclic ether group of the type —$R^X$—O—$R^Y$ or $[(CH_2)_xO]_Y(CH_2)_Z$ (x=2-3, y=3-8, z=2-5) respectively, and each of the other three R groups; a linear or branched, saturated or unsaturated $C_1$ to $C_9$ alkyl; a saturated or unsaturated carbocyclic group; a group of formula $CO_2R_5$ or $(CH_2)_nOH$ wherein $R_5$ is independently hydrogen or a linear or branched, saturated or unsaturated $C_1$ to $C_9$ alkyl and n=1-6; a saturated or unsaturated heterocyclic or heteroaliphatic group with one or more atoms selected from O, N and S, wherein said carbocyclics, heterocyclics and heteroaliphatics are optionally substituted by one or more linear or branched, saturated or unsaturated $C_1$ to $C_9$ alkyls; an ether group —$R^x$—O—$R^Y$ or $[(CH_2)_xO]_y(CH_2)_z$ (x=2-3, y=3-8, z=2-5), wherein $R^x$ and $R^Y$ are independently linear or branched, saturated or unsaturated $C_1$ to $C_9$ alkyl, or saturated or unsaturated carbocyclics, any of which alkyl and/or carbocyclic groups may be substituted or unsubstituted, provided that when the tridentate chelator is of the type of formula (1), when $R_1$ is —$R^x$—O—$R^Y$ wherein $R^Y$ is substituted, and $R_2$, $R_3$, and $R_4$ are each H, $R^Y$ is not substituted apically by a further tris(pyrazolyl)methane moiety; and when $R_1$ is —$R^x$—O—$R^Y$ and $R_2$, $R_3$ and $R_4$ are each H, $R_1$ cannot be —$CH_2$—O—$CH_2$-(p-$^tBu$-$C_6H_4$).

8. A tricarbonyl complex of a radioisotope of Tc or Re bound to a tridentate chelator according to claim 1.

9. The tricarbonyl complex according to claim 8 wherein the radioisotope is $^{99m}Tc$.

10. A composition comprising a tridentate chelator according to claim 1 and sodium boranocarbonate, sodium borate and sodium carbonate.

11. A composition according to claim 10, which is in lyophilised form.

12. A composition according to claim 10, further including a transfer ligand.

13. A composition according to claim 12, wherein the transfer ligand is selected from tartrate, gluconate, citrate or glucoheptonate salts.

14. A composition comprising a tridentate chelator according to claim 1 and a filler material.

15. A composition according to claim 14, wherein the filler material is inositol, lactose or saccharose.

16. A composition according to claim 14, further comprising an anti-oxidant.

17. A composition according to claim 16, wherein the anti-oxidant is selected from gentisic acid, ascorbic acid or methionine.

18. A process for the preparation of a tricarbonyl complex according to claim 8 or claim 9, comprising contacting a compound of the formula $[M(X)_3(CO)_3]^+$, wherein M=Tc or Re and X=$H_2O$, MeOH or a halogen, with a tridentate chelator according to any of claims 1-8 in an alcoholic or aqueous solvent, or with a composition according to any of claims 14-17, at a pH of about 6 or less.

19. A process according to claim 18 wherein the alcoholic solvent is ethanol.

20. A tricarbonyl complex according to claim 8 for use in diagnosis.

21. A tricarbonyl complex according to claim 20 wherein the diagnosis involves myocardial imaging.

22. Tridentate chelators according to claim 1, wherein $R^1$ is a linear ether group of the type $R^x$—O—$R^Y$, wherein $R^x$ and $R^Y$ are $C_1$ to $C_9$ alkyl.

\* \* \* \* \*